United States Patent
Diaz et al.

(10) Patent No.: US 7,348,449 B2
(45) Date of Patent: Mar. 25, 2008

(54) LIGAND ANTAGONISTS OF RAR RECEPTORS AND PHARMACEUTICAL/COSMETIC APPLICATIONS THEREOF

(75) Inventors: Philippe Diaz, Nice (FR); Catherine Raffin, Antibes (FR); Thibaud Biadatti, Opio (FR)

(73) Assignee: Galderma Research & Development, Biot (FR)

( * ) Notice: Subject to any disclaimer, the term of this patent is extended or adjusted under 35 U.S.C. 154(b) by 365 days.

(21) Appl. No.: 11/116,344

(22) Filed: Apr. 28, 2005

(65) Prior Publication Data

US 2005/0234131 A1   Oct. 20, 2005

Related U.S. Application Data

(63) Continuation of application No. PCT/EP03/14860, filed on Nov. 18, 2003.

(60) Provisional application No. 60/430,640, filed on Dec. 4, 2002.

(30) Foreign Application Priority Data

Nov. 18, 2002   (FR)   .................................... 02 14391

(51) Int. Cl.
  *C07C 69/76*   (2006.01)
  *C07C 59/76*   (2006.01)
  *C07C 233/00*  (2006.01)
  *A01N 47/10*   (2006.01)
  *A01N 37/10*   (2006.01)

(52) U.S. Cl. ...................... 560/101; 560/102; 562/460; 562/461; 564/180; 564/181; 514/476; 514/510; 514/569

(58) Field of Classification Search ...................... None
  See application file for complete search history.

(56) References Cited

U.S. PATENT DOCUMENTS 5,489,584 A * 2/1996 Vuligonda et al. .......... 514/188

FOREIGN PATENT DOCUMENTS

EP   0 931 786 A2   7/1999
FR   2 779 720 A1   12/1999

OTHER PUBLICATIONS

CAS online citation, 125:195216 [retrieved Oct. 3, 2007] from CAPLUS on STN, Columbus, OH, USA.*
French Search Report Corresponding to FR 02/14391, Issued on Jul. 29, 2003, 2 Pages International Search Report Corresponding to PCT/EP 03/14860, Issued on May 19, 2004, 3 Pages.

* cited by examiner

*Primary Examiner*—Karl Puttlitz
(74) *Attorney, Agent, or Firm*—Buchanan, Ingersoll & Rooney, PC

(57) ABSTRACT

Novel ligand antagonists of the RAR receptors have the following structural formula (I):

Figure 1:
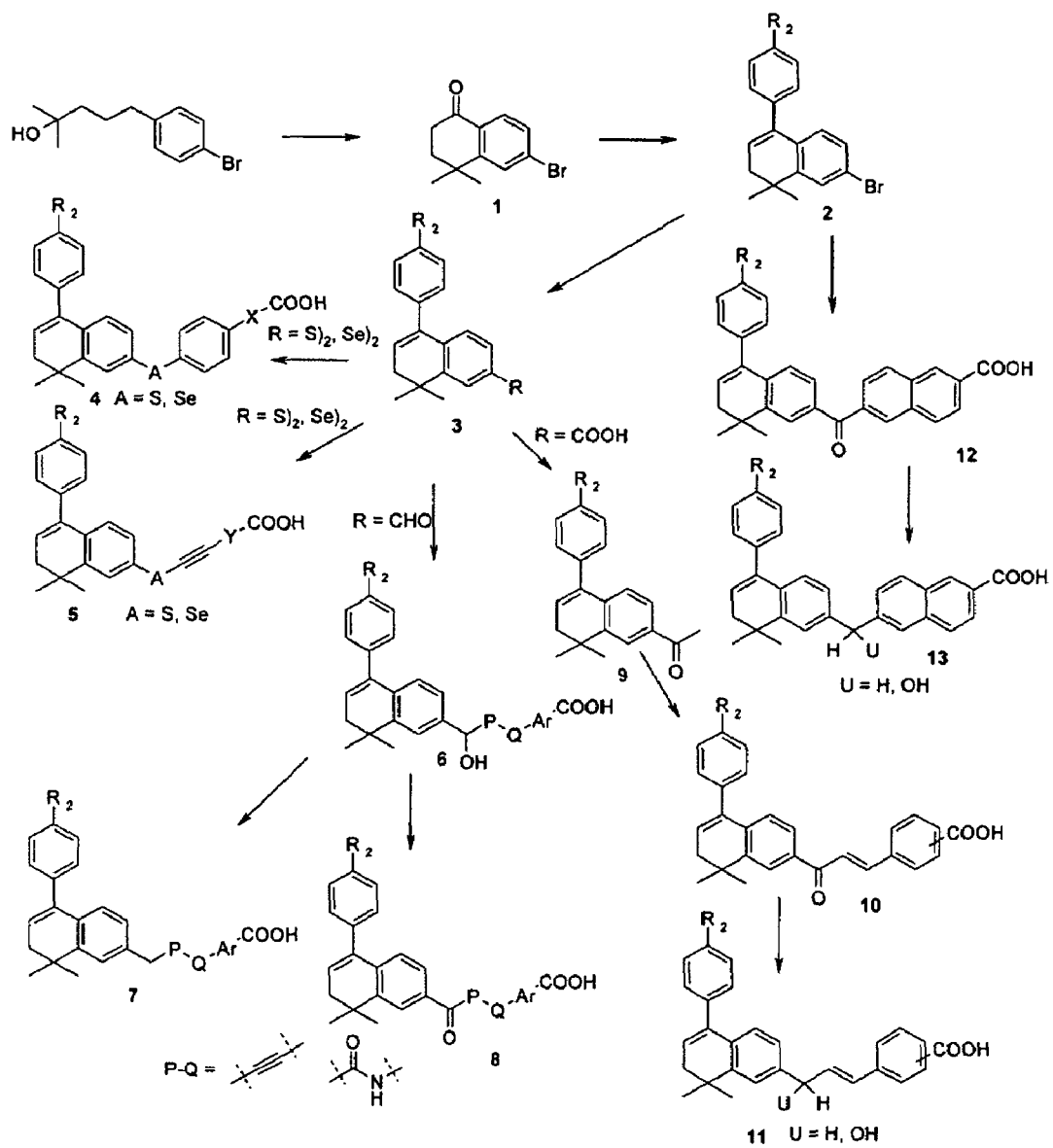

in which A is a $CH_2$, CHOH, C=O or C=N—OH radical or a sulfur or selenium atom; B is a radical selected from among those of formulae (a) to (f):
(a)
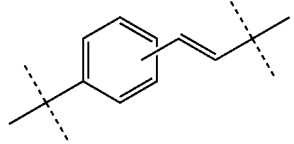
(b)
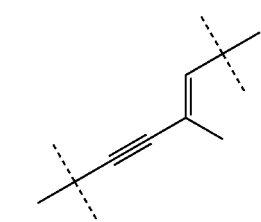
(c)
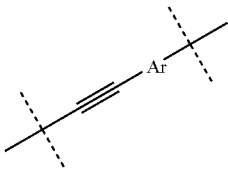
(d)
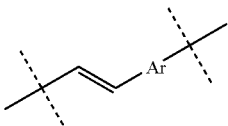
(e)
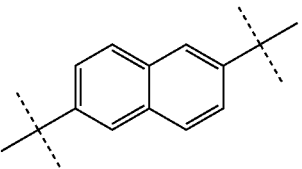
-continued
(f)
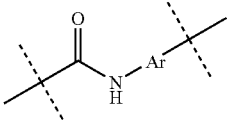
and Ar is a radical selected from among those of formulae (g) to (i):
(g)
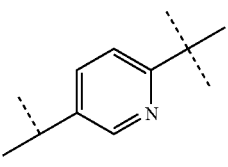
(h)
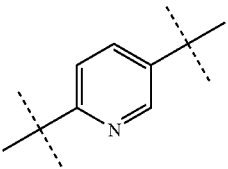
(i)
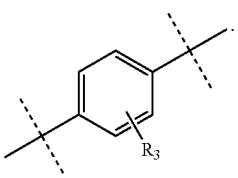
43 Claims, 1 Drawing Sheet

LIGAND ANTAGONISTS OF RAR RECEPTORS AND PHARMACEUTICAL/COSMETIC APPLICATIONS THEREOF

CROSS-REFERENCE TO PRIORITY/PCT/PROVISIONAL APPLICATIONS

This application claims priority under 35 U.S.C. § 119 of FR 02/14391, filed Nov. 18, 2002, and of provisional application Ser. No. 60/430,640, filed Dec. 4, 2002, and is a continuation of PCT/EP 2003/014860, filed Nov. 18, 2003 and designating the United States (published in the English language on Jun. 3, 2004 as WO 2004/046096 A3), each hereby expressly incorporated by reference and each assigned to the assignee hereof.

BACKGROUND OF THE INVENTION

1. Technical Field of the Invention

The present invention relates to novel ligands that are antagonists of the RAR receptors. This invention also relates to a process for preparing such novel ligands and to their formulation into pharmaceutical compositions for use in human or veterinary medicine, or, alternatively, into cosmetic compositions.

2. Description of Background and/or Related and/or Prior Art

Compounds with activity of retinoid type (vitamin A and its derivatives) are widely described in the literature as having activity in cell proliferation and differentiation processes. These properties give this class of compounds great potential in the treatment or prevention of numerous pathologies, and more particularly in dermatology and cancer. Many biological effects of retinoids are mediated by modulating the nuclear retinoic acid receptors (RAR).

The RAR receptors activate transcription by binding to DNA sequence elements, known as RAR response elements (RARE), in the form of a heterodimer with the retinoid X receptors (known as RXRs).

Three subtypes of human RARs have been identified and described: RARα, RARβ and RARγ.

The prior art includes a large number of chemical compounds with inhibitory activity on receptors of RAR type. Among the prior art references that may be mentioned, for example, are U.S. Pat. No. 6,150,413, which describes triaromatic compounds, U.S. Pat. No. 6,214,878, which describes stilbene compounds, and U.S. Pat. No. 6,218,128, which describes a family of bicyclic or tricyclic molecules.

SUMMARY OF THE INVENTION

Novel compounds have now been invented that are antagonists of the retinoic acid receptors.

Thus, the present invention features novel compounds having the structural formula (I) below:

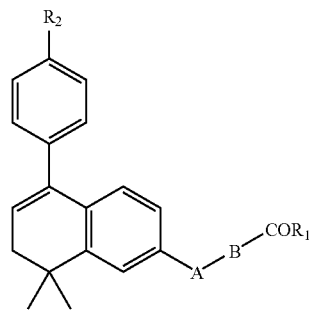

(I)

in which A is a $CH_2$, CHOH, C=O or C=N—OH radical or a sulfur or selenium atom; B is a radical selected from among those of formulae (a) to (f):

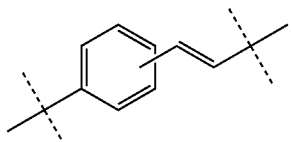

(a)

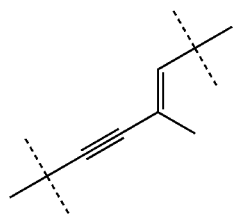

(b)

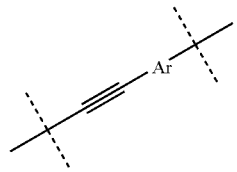

(c)

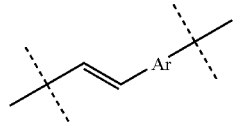

(d)

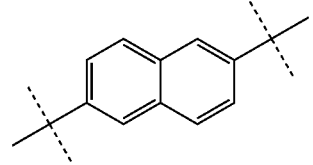

(e)

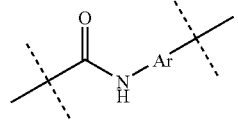

(f)

Ar is a radical selected from among those of formulae (g) to (i):

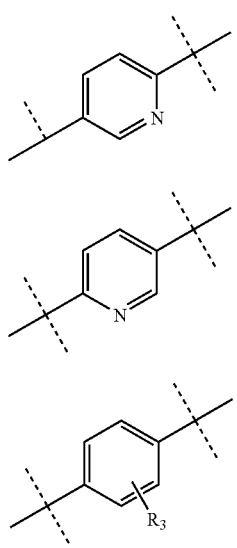
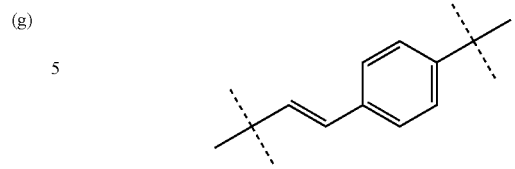

wherein $R_3$ is as defined below; $R_1$ is a radical —OH, —$OR_4$, —$NHR_5$ or $NR_5R_6$, wherein $R_4$, $R_5$ and $R_6$ are as defined below; $R_2$ is a hydrogen, fluorine, chlorine or bromine atom, a linear or branched alkyl radical having 1 to 5 carbon atoms, a $CF_3$, $OR_7$, $SR_7$, $NHR_8$, $NR_8R_9$, 2-naphthyl, 2-pyridyl, 3-pyridyl, 4-pyridyl, 2-thiophenyl, $CH_2OR_{10}$ or $CH_2NR_{11}R_{12}$ radical or a phenyl radical which is unsubstituted or substituted with at least one fluorine atom or with a methyl, ethyl, isopropyl, tert-butyl or $CF_3$ radical, wherein $R_7$, $R_8$, $R_9$, $R_{10}$, $R_{11}$, and $R_{12}$ are as defined below; $R_3$ is a hydrogen, fluorine or chlorine atom or a radical OH, $OR_{13}$, $CF_3$ or $NR_{14}R_{15}$, wherein $R_{13}$, $R_{14}$ and $R_{15}$ are as defined below; $R_4$ is a linear or branched alkyl radical having 1 to 4 carbon atoms; $R_5$ is a hydrogen atom, an OH group or a linear or branched alkyl radical having 1 to 4 carbon atoms; $R_6$ is a linear or branched alkyl radical having 1 to 4 carbon atoms; $R_7$ is a hydrogen atom, a linear or branched alkyl radical having 1 to 6 carbon atoms, a radical $CH_2OR_{16}$ or a benzyl radical which is unsubstituted or substituted with at least one halogen atom, preferably an fluorine atom, or with a methyl, ethyl, isopropyl, tert-butyl or $CF_3$ radical, wherein $R_{16}$ is as defined below; $R_8$, $R_9$, $R_{11}$, $R_{12}$, $R_{14}$ and $R_{15}$, which may be identical or different, are each a hydrogen atom, a linear or branched alkyl radical having 1 to 4 carbon atoms, (C=O)—$R_{17}$ or (C=O)—$OR_{17}$, wherein $R_{17}$ is as defined below; $R_{10}$ s a linear or branched alkyl radical having 1 to 4 carbon atoms or a benzyl or phenyl radical optionally substituted by one halogen atom, preferably one fluorine atom, or by one alkyl radical having 1 to 3 carbon atoms; $R_{13}$ is a methyl, ethyl or acetyl radical; $R_{16}$ is a methyl, ethyl or $CH_2CH_2OCH_3$ radical; $R_{17}$ is a hydrogen atom or a linear or branched alkyl radical having 1 to 4 carbon atoms; and the stereoisomers and optical or geometrical isomers thereof, pure or in admixture in all proportions, and the salts obtained with a pharmaceutically acceptable acid or base, and also mixtures of said compounds of formula (I), with the proviso that, when A is a C=O radical, then B cannot have the formula (d):

It will be appreciated that the invention embraces optical isomers of the compounds of formula (I) as well as mixtures thereof including racemic mixtures. The invention also embraces stereoisomers of the compounds of formula (I), including mixtures thereof.

When the compounds according to the invention are in the form of a salt, it is preferably an alkali metal or alkaline-earth metal salt, or alternatively a zinc salt or salts of an organic amine.

DETAILED DESCRIPTION OF BEST MODE AND SPECIFIC/PREFERRED EMBODIMENTS OF THE INVENTION

According to the present invention:

The term "alkyl radical having from 1 to 4 carbon atoms" preferably means methyl, ethyl, propyl, isopropyl, butyl, tert-butyl or isobutyl.

The term "alkyl radical having from 1 to 5 carbon atoms" preferably means methyl, ethyl, n-propyl, isopropyl, n-butyl, tert-butyl, isobutyl, n-pentyl or 2,2-dimethylpropyl.

The term "alkyl radical having from 1 to 6 carbon atoms" preferably means methyl, ethyl, n-propyl, isopropyl, n-butyl, tert-butyl, isobutyl, n-pentyl, 2,2-dimethylpropyl or n-hexyl radicals.

In one preferred embodiment, the compounds of formula (I) are those wherein A is a CHOH or C=O radical or a selenium atom, the other substituents remaining as previously defined.

In another preferred embodiment, the compounds of formula (I) are those wherein $R_1$ is a radical —OH, the other substituents remaining as previously defined.

In another preferred embodiment, the compounds of formula (I) are those in wherein $R_2$ is a linear or branched alkyl radical having 1 to 5 carbon atoms, a $OR_7$, or $NR_8R_9$ radical, the other substituents remaining as previously defined.

Among the compounds corresponding to formula (I) above, mention may be made of the following, alone or in admixture:

1. 4-(8,8-dimethyl-5-p-tolyl-7,8-dihydro-2-naphthylselanyl-ethynyl)benzoic acid
2. 5-(8,8-dimethyl-5-p-tolyl-7,8-dihydro-2-naphthylselanyl)-3-methylpent-2-en4-ynoic acid
3. 4-[5-(4-tert-butylphenyl)-8,8-dimethyl-7,8-dihydro-2-naphthylselanylethynyl]benzoic acid
4. 5-[5-(4-tert-butylphenyl)-8,8-dimethyl-7,8-dihydro-2-naphthylselanyl]-3-methylpent-2-en4-ynoic acid
5. 4-(8,8-dimethyl-5-p-tolyl-7,8-dihydro-2-naphthylselanyl-ethynyl)-2-methoxybenzoic acid
6. 4-(8,8-dimethyl-5-p-tolyl-7,8-dihydro-2-naphthylselanyl-ethynyl)-2-hydroxybenzoic acid
7. 4-[5-(4-methoxyphenyl)-8,8-dimethyl-7,8-dihydro-2-naphthylselanylethynyl]benzoic acid
8. 6-(8,8-dimethyl-5-p-tolyl-7,8-dihydro-2-naphthyl-selanylethynyl)nicotinic acid
9. 4-(8,8-dimethyl-5-p-tolyl-7,8-dihydro-2-naphthylselanyl-ethynyl)-2-fluorobenzoic acid 10. (E)-3-[4-(8,8-dimethyl-5-p-tolyl-7,8-dihydro-2-naphthylselanyl)phenyl]acrylic acid
11. (Z)-3-[3-(8,8-dimethyl-5-p-tolyl-7,8-dihydro-2-naphthylselanyl)phenyl]acrylic acid
12. 3-{4-[5-(4-tert-butylphenyl)-8,8-dimethyl-7,8-dihydro-2-naphthylselanyl]phenyl}acrylic acid
13. 3-{3-[5-(4-tert-butylphenyl)-8,8-dimethyl-7,8-dihydro-2-naphthylselanyl]phenyl}acrylic acid
14. 6-(8,8-dimethyl-5-p-tolyl-7,8-dihydro-2-naphthylselanyl)naphthalene-2-carboxylic acid
15. 4-[3-(8,8-dimethyl-5-p-tolyl-7,8-dihydro-2-naphthyl)-3-hydroxyprop-1-ynyl]benzoic acid
16. 4-[3-(8,8-dimethyl-5-p-tolyl-7,8-dihydro-2-naphthyl)-3-hydroxyprop-1-ynyl]-2-hydroxybenzoic acid
17. 4-{3-[5-(4-ethoxymethoxyphenyl)-8,8-dimethyl-7,8-dihydro-2-naphthyl]-3-hydroxyprop-1-ynyl}benzoic acid
18. 4-{3-[5-(4-benzyloxyphenyl)-8,8-dimethyl-7,8-dihydro-2-naphthyl]-3-hydroxyprop-1-ynyl}benzoic acid
19. 4-{3-[5-(4-dimethylaminophenyl)-8,8-dimethyl-7,8-dihydro-2-naphthyl]-3-hydroxyprop-1-ynyl}benzoic acid
b 20. 4-[3-(8,8-dimethyl-5-p-tolyl-7,8-dihydro-2-naphthyl)-3-oxoprop-1-ynyl]benzoic acid
21. 4-[3-(8,8-dimethyl-5-p-tolyl-7,8-dihydro-2-naphthyl)-3-hydroxypropenyl]benzoic acid
22. 6-[(8,8-dimethyl-5-p-tolyl-7,8-dihydro-2-naphthyl)-hydroxymethyl]naphthalene-2-carboxylic acid
23. 6-(8,8-dimethyl-5-p-tolyl-7,8-dihydro-2-naphthylcarbonyl)naphthalene-2-carboxylic acid
24. 4-[2-(8,8-dimethyl-5-p-tolyl-7,8-dihydro-2-naphthyl)-2-oxoacetylamino]benzoic acid
25. 4-[2-(8,8-dimethyl-5-p-tolyl-7,8-dihydro-2-naphthyl)-2-hydroxyacetylamino]benzoic acid
26. ethyl 4-[3-(8,8-dimethyl-5-p-tolyl-7,8-dihydro-2-naphthyl)-3-hydroxyprop-1-ynyl]benzoate
27. isobutyl 4-[3-(8,8-dimethyl-5-p-tolyl-7,8-dihydro-2-naphthyl)-3-hydroxyprop-1-ynyl]benzoate
28. 4-[3-(8,8-dimethyl-5-p-tolyl-7,8-dihydro-2-naphthyl)-3-hydroxyprop-1-ynyl]-N-hydroxybenzamide
29. 4-[3-(8,8-dimethyl-5-p-tolyl-7,8-dihydro-2-naphthyl)-3-hydroxyprop-1-ynyl]-N,N-dimethylbenzamide
30. 4-[3-(8,8-dimethyl-5-p-tolyl-7,8-dihydro-2-naphthyl)-3-hydroxyprop-1-ynyl]-N-methylbenzamide
31. 4-[3-(8,8-dimethyl-5-p-tolyl-7,8-dihydro-2-naphthyl)-3-hydroxyprop-1-ynyl]-N-isobutylbenzamide
32. 4-[3-(8,8-dimethyl-5-p-tolyl-7,8-dihydro-2-naphthyl)-3-hydroxyprop-1-ynyl]-N-isobutyl-N-methylbenzamide
33. isobutyl 4-(8,8-dimethyl-5-p-tolyl-7,8-dihydro-2-naphthylselanylethynyl)benzoate
34. 4-(5-biphenyl-4-yl-8,8-dimethyl-7,8-dihydro-2-naphthylselanylethynyl)benzoic acid
35. 4-[3-(5-biphenyl-4-yl-8,8-dimethyl-7,8-dihydro-2-naphthyl)-3-hydroxyprop-1-ynyl]benzoic acid
36. 4-{3-[8,8-dimethyl-5-(4-pyrid-2-ylphenyl)-7,8-dihydro-2-naphthyl]-3-hydroxyprop-1-ynyl}benzoic acid
37. 4-[8,8-dimethyl-5-(4-pyrid-2-ylphenyl)-7,8-dihydro-2-naphthylselanylethynyl]benzoic acid
38. 4-[8,8-dimethyl-5-(4-thiophen-2-ylphenyl)-7,8-dihydro-2-naphthylselanylethynyl]benzoic acid
39. 4-{3-hydroxy-3-[5-(4-methoxymethylphenyl)-8,8-dimethyl-7,8-dihydro-2-naphthyl]prop-1-ynyl}benzoic acid
40. 4-[5-(4-methoxymethylphenyl)-8,8-dimethyl-7,8-dihydro-2-naphthylselanylethynyl]benzoic acid
41. 4-[8,8-dimethyl-5-(4-phenoxymethylphenyl)-7,8-dihydro-2-naphthylselanylethynyl]benzoic acid
42. 4-{3-[8,8-dimethyl-5-(4-phenoxymethylphenyl)-7,8-dihydro-2-naphthyl]-3-hydroxyprop-1-ynyl}benzoic acid
43. 4-(3-{5-[4-(4-fluorophenoxymethyl)phenyl]-8,8-dimethyl-7,8-dihydro-2-naphthyl}-3-hydroxyprop-1-ynyl)benzoic acid
44. 4-{5-[4-(4-fluorophenoxymethyl)phenyl]-8,8-dimethyl-7,8-dihydro-2-naphthylselanylethynyl}benzoic acid
45. 4-[5-(4-dimethylaminomethylphenyl)-8,8-dimethyl-7,8-dihydro-2-naphthylselanylethynyl]benzoic acid
46. 4-{3-[5-(4-dimethylaminomethylphenyl)-8,8-dimethyl-7,8-dihydro-2-naphthyl]-3-hydroxyprop-1-ynyl}benzoic acid
47. 4-[3-(5-{4-[(acetylmethylamino)methyl]phenyl}-8,8-dimethyl-7,8-dihydro-2-naphthyl)-3-hydroxyprop-1-ynyl]benzoic acid
48. 4-(5-{4-[(acetylmethylamino)methyl]phenyl}-8,8-dimethyl-7,8-dihydro-2-naphthylselanylethynyl)benzoic acid
49. 4-[5-(4-acetylaminophenyl)-8,8-dimethyl-7,8-dihydro-2-naphthylselanylethynyl]benzoic acid
50. 4-{3-[5-(4-tert-butoxycarbonylaminophenyl)-8,8-dimethyl-7,8-dihydro-2-naphthyl]-3-hydroxyprop-1-ynyl}benzoic acid
51. 4-(3-{5-[4-(tert-butoxycarbonylmethylamino)phenyl]-8,8-dimethyl-7,8-dihydro-2-naphthyl}-3-hydroxyprop-1-ynyl)benzoic acid
52. 4-{5-[4-(tert-butoxycarbonylmethylamino)phenyl]-8,8-dimethyl-7,8-dihydro-2-naphthylselanylethynyl}benzoic acid
53. 4-[5-(4-tert-butoxycarbonylaminophenyl)-8,8-dimethyl-7,8-dihydro-2-naphthylselanylethynyl]benzoic acid
54. 4-{5-[4-(4-fluorobenzyloxy)phenyl]-8,8-dimethyl-7,8-dihydro-2-naphthylselanylethynyl}benzoic acid
55. 4-(3-{5-[4-(4-fluorobenzyloxy)phenyl]-8,8-dimethyl-7,8-dihydro-2-naphthyl}-3-hydroxyprop-1-ynyl)benzoic acid
56. 4-{3-[5-(4-benzylsulfanylphenyl)-8,8-dimethyl-7,8-dihydro-2-naphthyl]-3-hydroxyprop-1-ynyl}benzoic acid
57. 4-[5-(4-benzylsulfanylphenyl)-8, 8-dimethyl-7,8-dihydro-2-naphthylselanylethynyl]benzoic acid
58. 4-{3-hydroxy-3-[5-(4-thiophen-2-ylphenyl)-8,8-dimethyl-7,8-dihydro-2-naphthyl]prop-1-ynyl}benzoic acid
59. 4-{3-[5-(4-acetylaminophenyl)-8,8-dimethyl-7,8-dihydro-2-naphthyl]-3-hydroxyprop-1-ynyl}benzoic acid
60. (S)-4-[3-(8,8-dimethyl-5-p-tolyl-7,8-dihydro-2-naphthyl)-3-hydroxyprop-1-ynyl]benzoic acid
61. (R)-4-[3-(8,8-dimethyl-5-p-tolyl-7,8-dihydro-2-naphthyl)-3-hydroxyprop-1-ynyl]benzoic acid.

The present invention also features processes for preparing the compounds of formula (I), in particular according to the reaction schemes shown in the FIGURE of Drawing.

It will be understood that the compounds of formula (I) can be prepared from known compounds by the application or adaptation of known methods.

6-Bromo4,4-dimethyltetralone 1 is obtained by electrophilic cyclization of 4-(4-bromophenyl)-2-methylpentanol followed by oxidation of the benzylic position. The addition of an organometallic reagent, for example an arylmagnesium halide, followed by a dehydration reaction, gives the compounds of general structure 2. The formation of a lithiated reagent or of a Grignard reagent provides access to the products of general formula 3, by trapping the anion with sulfur or selenium (R=S or Se), dimethylformamide (R=CHO) or carbon dioxide (R=COOH).

The compounds of structure 4 are then obtained, from the corresponding disulfides or diselenides 3, by reduction to sulfide or selenide, for example using sodium borohydride, followed by coupling with an aryl iodide corresponding to the acid portion, in the presence of bis(bipyridyl)nickel dibromide, followed by saponification of the esters obtained.

The compounds of structure 5 are obtained after bromination of the disulfide or diselenide function, followed by addition of a true alkyne function in the presence of copper iodide. The esters obtained are then saponified.

The compounds of structure 6 are obtained by nucleophilic addition of a cyanide ion or of an ethynyl ion to the aldehyde function of 3, followed by formation of an amide bond (P-Q=(C=O)—NH) or alternatively by Sonogashira coupling with a corresponding aryl halide (P-Q=alkyne). The compounds of structure 7 may then be obtained by deoxygenation, for example with triethylsilyl hydride, and the compounds of formula 8 by oxidation of the alcohol function to a carbonyl, for example using manganese oxide.

The methyl ketones of the type 9 may be obtained after reacting the carboxylic acids 3 with methyllithium. The chalcones of general structure 10 may then be produced after reacting the compounds of type 9 with corresponding benzaldehydes in the presence of strong bases, for instance potassium hydroxide. The reduction of the carbonyl group then provides access to the compounds of structure 11 (U=OH), and deoxygenation of these compounds can lead to compounds of the type 11 (U=H).

The compounds of general structure 12 may be obtained after generating an organometallic reagent, for example an organozinc reagent, from the aryl bromides of structure 2, and nucleophilic attack on a corresponding acid chloride. Reduction of the carbonyl group then provides access to the compounds of structure 13 (U=OH), and deoxygenation of these compounds can lead to compounds of the type 13 (U=H).

The compounds according to the invention have inhibitory properties on RAR-type receptors. This RAR-receptor inhibitory activity is measured in a test of transactivation by means of the dissociation constant Kdapp (apparent) and the $IC_{50}$ (concentration that inhibits 50% of the reference agonist activity).

According to the invention, the expression "inhibitor of RAR-type receptors" means any compound which, for at least one of the RAR subtypes, has a dissociation constant Kdapp of less than or equal to 1 μM, and an $IC_{50}$ value ≦100 nM, in a transactivation test as described in Example 26.

The preferred compounds of the present invention have, for at least one of the RAR subtypes, a dissociation constant Kdapp of less than or equal to 500 nM and advantageously less than or equal to 100 nM, and an $IC_{50}$≦25 nM.

The present invention also features the compounds of formula (I) as described above, as medicinal products.

The compounds according to the invention are particularly suitable in the following fields of treatment:

1) for treating dermatological complaints, disorders or afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;

2) for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;

3) for treating other dermatological complaints or afflictions having an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;

4) for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basocellular and spinocellular epithelioma, and also any cutaneous precancerous lesion such as keratoacanthomas;

5) for treating other dermatological disorders such as immune dermatoses, such as lupus erythematosus, immune bullous diseases and collagen diseases, such as scleroderma;

6) in the treatment of dermatological or general complaints or afflictions having an immunological component;

7) for treating certain ophthalmological disorders, especially corneopathies, 8) for preventing or curing the stigmata of epidermal and/or dermal atrophy induced by local or systemic corticosteroids, or any other form of cutaneous atrophy, 9) in the treatment of any cutaneous or general complaint or affliction of viral origin, 10) in the treatment of skin disorders caused by exposure to UV radiation, and also for repairing or combating aging of the skin, whether photoinduced or chronological aging, or for reducing pigmentations and actinic keratosis, or any pathology associated with chronological or actinic aging, such as xerosis;

11) for combating sebaceous function disorders, such as the hyperseborrhoea of acne or simple seborrhoea;

12) for preventing or treating cicatrization disorders, or for preventing or repairing stretch marks, or alternatively for promoting cicatrization;

13) in the treatment of pigmentation disorders, such as hyperpigmentation, melasma, hypopigmentation or vitiligo;

14) in the treatment of lipid metabolism complaints or afflictions, such as obesity, hyperlipidaemia, or non-insulin-dependent diabetes;

15) in the treatment of inflammatory complaints or afflictions, such as arthritis;

16) in the treatment or prevention of cancerous or precancerous conditions;

17) in the prevention or treatment of alopecia of various origins, especially alopecia caused by chemotherapy or radiation;

18) in the treatment of disorders of the immune system, such as asthma, type I sugar diabetes, multiple sclerosis or other selective dysfunctions of the immune system; and 19) in the treatment of complaints or afflictions of the cardiovascular system, such as arteriosclerosis or hypertension.

The present invention also features pharmaceutical compositions comprising, formulated into a physiologically acceptable medium, at least one compound of formula (I) as defined above.

The present invention also features novel medicinal compositions especially suited for treating the abovementioned complaints, conditions or afflictions which are characterized in that they comprise, formulated into a pharmaceutically acceptable support that is compatible with the mode of administration selected for the particular composition, at least one compound of formula (I), an optical isomer thereof or a salt thereof.

The compositions according to the invention may be administered orally, enterally, parenterally, topically or ocularly. The pharmaceutical composition is preferably packaged in a form that is suitable for topical or oral application.

Via the oral route, the composition may be in the form of tablets, gel capsules, dragees, syrups, suspensions, solutions, powders, granules, emulsions, suspensions of microspheres or nanospheres or lipid or polymer vesicles allowing a controlled release. Via the parenteral route, the composition may be in the form of solutions or suspensions for infusion or for injection.

The compounds according to the invention are generally administered at a daily dose of about 0.01 mg/kg to 100 mg/kg of body weight, in 1 to 3 dosage intakes.

The compounds are used systemically, at a concentration generally of from 0.001% to 10% by weight and preferably from 0.01% to 1% by weight relative to the weight of the composition.

Via the topical route, the pharmaceutical compositions according to the invention are more particularly suited for treating the skin and mucous membranes and may be in liquid, pasty or solid form, and more particularly in the form of ointments, creams, milks, pomades, powders, impregnated pads, syndets, solutions, gels, sprays, mousses, suspensions, sticks, shampoos or washing bases. They may also be in the form of suspensions of microspheres or nanospheres or of lipid or polymer vesicles or gelled or polymer patches allowing a controlled release.

The compounds are used topically at a concentration generally of from 0.001% to 10% by weight and preferably from 0.01% to 1% by weight, relative to the total weight of the composition.

The compounds of formula (I) according to the invention also find an application in cosmetics, in particular in body and hair hygiene and especially for treating acne-prone skin, for promoting regrowth of the hair or for limiting hair loss, for combating the greasy appearance of the skin or the hair, in protection against the harmful aspects of sunlight or in the treatment of physiologically dry skin, and for preventing and/or combating photoinduced or chronological aging.

This invention thus also features compositions comprising, formulated into a cosmetically acceptable support, at least one of the compounds of formula (I).

This invention also features a cosmetic regime or regimen utilizing a composition comprising at least one compound of formula (I) for preventing and/or treating the signs of aging and/or dry skin.

The present invention also features the cosmetic use of a composition comprising at least one compound of formula (I) for body or hair hygiene.

The cosmetic composition according to the invention containing, in a cosmetically acceptable support, at least one compound of formula (I) or an optical or geometrical isomer thereof or a salt thereof, may be especially in the form of a cream, a milk, a gel, suspensions of microspheres or nanospheres or lipid or polymer vesicles, impregnated pads, solutions, sprays, mousses, sticks, soaps, shampoos or washing bases.

The concentration of compound of formula (I) in the cosmetic composition is preferably from 0.001% to 3% by weight relative to the total weight of the composition.

The pharmaceutical and cosmetic compositions as described above may also contain inert additives, or even pharmacodynamically active additives as regards the pharmaceutical compositions, or combinations of these additives, and especially:

wetting agents;

flavor enhancers;

preservatives such as para-hydroxybenzoic acid esters;

stabilizers;

moisture regulators;

pH regulators;

osmotic pressure modifiers;

emulsifiers;

UV-A and UV-B screening agents;

antioxidants such as a-tocopherol, butylhydroxyanisole, butylhydroxytoluene, superoxide dismutase, ubiquinol or certain metal-chelating agents;

depigmenting agents such as hydroquinone, azelaic acid, caffeic acid or kojic acid;

emollients;

moisturizers, for instance glycerol, PEG 400, thiamorpholinone and its derivatives or urea;

antiseborrhoeic or antiacne agents, such as S-carboxymethylcysteine, S-benzylcysteamine, salts thereof or derivatives thereof, or benzoyl peroxide;

antibiotics, for instance erythromycin and its esters, neomycin, clindamycin and its esters, and tetracyclines;

antifungal agents such as ketoconazole or poly-4,5-methylene-3-isothiazolidones;

agents for promoting regrowth of the hair, for instance Minoxidil (2,4-diamino-6-piperidinopyrimidine 3-oxide) and its derivatives, Diazoxide (7-chloro 3-methyl-1,2,4-benzothiadiazine 1,1-dioxide) and Phenytoin (5,4-diphenylimidazolidine-2,4-dione);

non-steroidal anti-inflammatory agents;

carotenoids and especially β-carotene;

anti-psoriatic agents such as anthralin and its derivatives;

eicosa-5,8,11,14-tetraynoic acid and eicosa-5,8,11-triynoic acid, and esters and amides thereof;

retinoids, i.e., natural or synthetic RXR receptor ligands;

corticosteroids or oestrogens;

α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;

ion-channel blockers such as potassium-channel blockers;

or alternatively, more particularly for pharmaceutical compositions, in combination with medicinal products known to interfere with the immune system (for example cyclosporin, FK 506, glucocorticoids, monoclonal antibodies, cytokines or growth factors, etc.).

Needless to say, one skilled in the art will take care to select the optional compound(s) to be added to these compositions such that the advantageous properties intrinsically attached to the present invention are not, or are not substantially, adversely affected by the envisaged addition.

In order to further illustrate the present invention and the advantages thereof, the following specific examples of the preparation of active compounds of formula (I) are given, as well as the biological activities and specific formulations thereof, it being understood that same are intended only as illustrative and in nowise limitative. In said examples to follow, all parts and percentages are given by weight, unless otherwise indicated.

EXAMPLE 1

Synthesis of 4-(8,8-Dimethyl-5-p-tolyl-7,8-dihydro-2-naphthylselanylethynyl)benzoic acid a. Preparation of Methyl 4-ethynylbenzoate:

3.3 g (14.5 mmol) of methyl 4-iodobenzoate and 4.1 ml (29 mmol) of trimethylsilylacetylene are dissolved in 20 ml of triethylamine, and 1 g (1.4 mmol) of trans-dichlorobis(triphenylphosphine)palladium and 0.55 g (2.8 mmol) of copper iodide are then added. The reaction medium is stirred for 24 hours, filtered through Celite and rinsed with ethyl acetate. The brown oil obtained (2.8 g; yield=96%) is dissolved in 30 ml of methanol and 6.6 g (48 mmol) of potassium carbonate are added. The medium is stirred for 48 hours and then concentrated to dryness. The residue obtained is purified by chromatography (eluent: 8/2 heptane/dichloromethane). An orange oil is obtained (1.8 g; yield=91%).

b. Preparation of 7-Bromo-1,1-dimethyl-1,2,3,4-tetrahydronaphthalene:

21.5 g (84 mmol) of 2-methyl-5-(4-bromophenyl)-2-pentanol are dissolved in 42 g of polyphosphoric acid. The reaction medium is heated at 60° C. for 9 hours and then hydrolysed and then extracted with ethyl acetate. The organic phase is treated with saturated sodium carbonate solution and then with sodium chloride solution. The residue obtained is purified by chromatography (eluent: 9/1 heptane/ethyl acetate). A viscous red oil is obtained (19.2 g; yield=77%).

c. Preparation of 6-Bromo-4,4-dimethyl-3,4-dihydro-2H-naphthalen-1-one:

A solution of 8.1 g (81 mmol) of chromium trioxide in 74 ml of acetic acid and 3.9 ml of water is added slowly to 14.3 g (60 mmol) of 7-bromo-1,1-dimethyl-1,2,3,4-tetrahydronaphthalene dissolved in 1.5 l of acetic acid. The reaction medium is stirred for 15 hours, reduced to a volume of 500 ml by concentration, hydrolysed with ice, extracted with ethyl ether and neutralized with 35% sodium hydroxide solution. The solid obtained is washed with heptane. A pink-white powder is obtained (8 g; 53%).

d. Preparation of 7-Bromo-1,1-dimethyl-4-para-tolyl-1,2-dihydronaphthalene:

5 g (20 mmol) of 6-bromo-4,4-dimethyl-3,4-dihydro-2H-naphthalen-1-one and 5.1 g (20 mmol) of magnesium bromide diethyl etherate are dissolved in 130 ml of tetrahydrofuran. The reaction medium is refluxed until the precipitate has disappeared, and 30 ml (30 mmol) of a 1M solution of para-tolylmagnesium bromide in ethyl ether are then added dropwise. The reaction medium is refluxed for 4 hours, hydrolysed with 1N hydrochloric acid solution and then extracted with ethyl ether. The brownish paste obtained is dissolved in 65 ml of toluene, and 0.14 g (0.73 mmol) of para-toluenesulfonic acid is then added. The reaction medium is refluxed for 45 minutes and then hydrolysed and extracted with ethyl ether. The residue obtained is purified by chromatography (eluent: 7/3 heptane/dichloromethane). A brown oil is obtained (3.2 g; yield=50%).

e. Preparation of Bis(8,8-dimethyl-5-para-tolyl-7,8-dihydro-2-naphthalene) diselenide:

1.5 g (4.9 mmol) of 7-bromo-1,1-dimethyl-4-para-tolyl-1,2-dihydro-naphthalene are dissolved in 30 ml of tetrahydrofuran at −78° C. 6.9 ml (11.6 mmol) of a 1.7M solution of tert-butyllithium are added dropwise. The reaction medium is stirred for 30 minutes while allowing the temperature to rise to 0° C. 0.42 g (5.3 mmol) of selenium is added portionwise. The reaction medium is stirred for 15 minutes at 0° C. and then for 30 minutes while allowing the temperature to rise to room temperature. 6 ml of 1N hydrochloric acid are added and the medium is then extracted with ethyl ether. The residue obtained is purified by chromatography (eluent: 95/5 heptane/dichloromethane). A yellow solid is obtained (0.8 g; yield=50%).

f. Preparation of Methyl 4-(8,8-dimethyl-5-p-tolyl-7,8-dihydro-2-naphthylselanylethynyl)benzoate:

0.785 g (1.2 mmol) of bis(8,8-dimethyl-5-p-tolyl-7,8-dihydro-2-naphthalene) diselenide is dissolved in 8 ml of tetrahydrofuran and 1.2 ml (1.2 mmol) of a 1M solution of dibromine in tetrahydrofuran are then added dropwise at −78° C. 15 minutes later, 1.4 g (7.3 mmol) of copper iodide and 17 ml of dimethylformamide are added. The reaction medium is stirred for 20 minutes while allowing the temperature to rise to 20° C. 0.32 g (2 mmol) of methyl 4-ethynylbenzoate (described in Example 1a) is added portionwise. The reaction medium is stirred for 24 hours, treated with ammonium chloride solution and extracted with ethyl acetate. The residue obtained is purified by chromatography (eluent: 8/2 heptane/dichloromethane). A yellow solid is obtained (0.46 g; yield=47%).

g. Synthesis of 4-(8,8-Dimethyl-5-p-tolyl-7,8-dihydro-2-naphthylselanylethynyl)benzoic acid:

0.46 g (0.95 mmol) of methyl 4-(8,8-dimethyl-5-p-tolyl-7,8-dihydro-2-naphthylselanylethynyl)benzoate is dissolved in 20 ml of tetrahydrofuran, 2 ml of ethanol and 1 ml of water, and 0.46 g (11 mmol) of lithium hydroxide monohydrate is then added. The reaction medium is refluxed for 15 hours, acidified with 2N hydrochloric acid solution and then extracted with ethyl acetate. The solid obtained is washed with a heptane/ethyl ether mixture (90/10) and then purified by chromatography (eluent: dichloromethane). An off-white powder is obtained (0.2 g; yield=45%).

$^1$H NMR (CDCl$_3$) 1.35 (s, 6H); 2.35 (d, 2H, 7.6 Hz); 2.39 (s, 3H); 5.97 (t,1H, 7.6 Hz); 7.02 (d, 1H, 13.2 Hz); 7.34-7.17 (M, 5H); 7.57-7.51 (M, 3H); 8.06 (d, 2H, 16 Hz).

EXAMPLE 2

Synthesis of 5-(8,8-Dimethyl-5-p-tolyl-7,8-dihydro-2-naphthylselanyl)-3-methylpent-2-en-4-ynoic acid a. Preparation of Methyl 3-methylpent-2-en-4-ynoate:

0.67 g (3 mmol) of palladium diacetate and 1.3 g (3 mmol) of tris(2,6-dimethoxyphenyl)phosphine are dissolved -in 300 ml of tetrahydrofuran. The reaction medium is stirred for 40 minutes and 11.4 g (102 mmol) of ethyl butynoate are then added dropwise. After 30 minutes, 11 g (112 mmol) of (trimethylsilyl)acetylene are added and the medium is then stirred for 15 hours and concentrated to dryness. The residue obtained is purified by chromatography (eluent: 7/3 heptane/dichloromethane). The orange-colored liquid obtained (22.4 g; yield=100%) is dissolved in 200 ml of ethanol, 200 ml of tetrahydrofuran and 20 ml of water. 11.9 g (204 mmol) of potassium fluoride are added portionwise and the medium is then stirred for 15 hours, treated with ammonium chloride solution and extracted with ethyl ether. The residue obtained is purified by chromatography (eluent: 7/3 pentane/dichloromethane). A yellow liquid is obtained (10.4 g; yield=74%).

b. Preparation of Methyl 5-(8,8-dimethyl-5-p-tolyl-7,8-dihydro-2-naphthylselanyl)-3-methylpent-2-en-4-ynoate:

In a manner similar to that of Example 1f, by reacting 0.3 g (0.46 mmol) of bis(8,8-dimethyl-5-p-tolyl-7,8-dihydro-2-naphthalene) diselenide with 0.46 ml (0.46 mmol) of a 1M solution of dibromine in tetrahydrofuran, 0.7 g (3.7 mmol)

of copper iodide, 7.5 ml of dimethylformamide and 0.13 g (0.92 mmol) of methyl 3-methylpent-2-en4-ynoate (described above). A yellow oil is obtained (0.24 g; yield=55%).

c. Synthesis of 5-(8,8-Dimethyl-5-p-tolyl-7,8-dihydro-2-naphthylselanyl)-3-methylpent-2-en-4-ynoic acid:

In a manner similar to that of Example 1g, by reacting 0.23 g (0.5 mmol) of methyl 5-(8,8-dimethyl-5-p-tolyl-7,8-dihydro-2-naphthylselanyl)-3-methylpent-2-en4-ynoate with 0.23 g (5.5 mmol) of lithium hydroxide monohydrate, a pale yellow solid is obtained (0.05 g; yield=23%; m.p.=166° C.).

$^1$H NMR (DMSO) 1.20 (s, 6H); 2.18 (s, 3H); 2.24 (s, 3H); 5.87 (s, 1H); 5.91 (s, 1H); 6.82 (d, 1H, 13.2 Hz); 7.14-7.06 (M, 4H); 7.26 (d, 1H, 12.8 Hz); 7.50 (s, 1H); 12.4 (s, 1H).

EXAMPLE 3

Synthesis of 4-[5-(4-tert-Butylphenyl)-8,8-dimethyl-7,8-dihydro-2-naphthylselanylethynyl]benzoic acid a. Preparation of 7-Bromo-4-(4-tert-butylphenyl)-1,1-dimethyl-1,2-dihydronaphthalene:

In a manner similar to that of Example 1d, by reacting 3.4 g (13.6 mmol) of 6-bromo-4,4-dimethyl-3,4-dihydro-2H-naphthalen-1-one with 3.5 g (13.6 mmol) of magnesium bromide diethyl etherate, 10.2 ml (20.4 mmol) of a 2M solution of 4-tert-butylphenylmagnesium bromide in ethyl ether and 96 mg (0.5 mmol) of para-toluenesulfonic acid, a brown solid is obtained (3.5 g; 70%).

b. Preparation of Bis[5-(4-tert-butylphenyl)-8,8-dimethyl-7,8-dihydro-2-naphthalene] diselenide:

In a manner similar to that of Example 1e, by reacting 2 g (5.4 mmol) of 7-bromo-4-(4-tert-butylphenyl)-1,1-dimethyl-1,2-dihydro-naphthalene with 7.6 ml (13 mmol) of a 1.7M solution of tert-butyllithium and 0.47 g (5.9 mmol) of selenium, a yellow solid is obtained (0.92 g; yield=46%).

c. Preparation of Methyl 4-[5-(4-tert-butylphenyl)-8,8-dimethyl-7,8-dihydro-2-naphthylselanylethynyl]benzoate:

In a manner similar to that of Example 1f, by reacting 0.30 g (0.41 mmol) of bis[5-(4-tert-butylphenyl)-8,8-dimethyl-7,8-dihydro-2-naphthalene] selenide with 0.4 ml (0.41 mmol) of a 1M solution of dibromine in tetrahydrofuran, 0.46 g (2.4 mmol) of copper iodide, 6 ml of dimethylformamide and 0.11 g (0.68 mmol) of methyl 4-ethynylbenzoate (described in Example 1a), a yellow oil is obtained (0.28 g; yield=78%).

d. Synthesis of 4-[5-(4-tert-Butylphenyl)-8,8-dimethyl-7,8-dihydro-2-naphthylselanylethynyl]benzoic acid:

In a manner similar to that of Example 1g, by reacting 0.28 g (0.5 mmol) of methyl 4-[5-(4-tert-butylphenyl)-8,8-dimethyl-7,8-dihydro-2-naphthylselanylethynyl]benzoate with 0.28 g (6.6 mmol) of lithium hydroxide monohydrate, a cream-colored powder is obtained (0.08 g; yield=30%; m.p. =231° C.).

$^1$H NMR (CDCl$_3$) 1.36 (s, 15H); 2.35 (d, 2H, 7.6 Hz); 5.99 (t, 1H, 7.6 Hz); 7.07 (d, 1H, 13.2 Hz); 7.57-7.26 (M, 8H); 8.06 (d, 1H, 13.6 Hz).

EXAMPLE 4

Synthesis of 5-[5-(4-tert-Butylphenyl)-8,8-dimethyl-7,8-dihydro-2-naphthylselanyl]-3-methylpent-2-en-4-ynoic acid a. Preparation of Methyl 5-[5-(4-tert-Butylphenyl)-8,8-dimethyl-7,8-dihydro-2-naphthylselanyl]-3-methylpent-2-en-4-ynoate:

In a manner similar to that of Example 3c, by reacting 0.30 g (0.41 mmol) of bis[5-(4-tert-butylphenyl)-8,8-dimethyl-7,8-dihydro-2-naphthalene] diselenide with 0.4 ml (0.41 mmol) of a 1M solution of dibromine in tetrahydrofuran, 0.46 g (2.4 mmol) of copper iodide, 6 ml of dimethylformamide and 0.11 g (0.68 mmol) of methyl 3-methylpent-2-en-4-ynoate (described in Example 2a), a yellow oil is obtained (0.19 g; yield=52%).

b. Synthesis of 5-[5-(4-tert-Butylphenyl)-8,8-dimethyl-7,8-dihydro-2-naphthylselanyl]-3-methylpent-2-en-4-ynoic acid:

In a manner similar to that of Example 3d, by reacting 0.19 g (0.37 mmol) of methyl 5-[5-(4-tert-butylphenyl)-8,8-dimethyl-7,8-dihydro-2-naphthylselanyl]-3-methylpent-2-en-4-ynoate with 0.19 g (4.5 mmol) of lithium hydroxide monohydrate, a cream-colored powder is obtained (0.06 g; yield=33%; m.p.=231° C.).

$^1$H NMR (CDCl$_3$) 1.36 (s, 15H); 2.34 (m, 5H); 5.99 (t, 1H, 7.6 Hz); 6.04 (m, 1H); 7.06 (d, 1H, 13.2 Hz); 7.27 (m, 3H); 7.39 (d, 2H, 13.6 Hz); 7.50 (m, 1H).

EXAMPLE 5

Synthesis of 4-(8,8-Dimethyl-5-p-tolyl-7,8-dihydro-2-naphthylselanylethynyl)-2-methoxybenzoic acid a. Preparation of Methyl 4-ethynyl-2-hydroxybenzoate:

5.5 g (20 mmol) of methyl 4-iodosalicylate and 2.3 g (24 mmol) of trimethylsilylacetylene are dissolved in 50 ml of triethylamine, and 0.7 g (1 mmol) of trans-dichlorobis(triphenylphosphine)palladium and 0.28 g (2 mmol) of copper iodide are then added. The reaction medium is stirred for 24 hours, treated with ammonium chloride solution and extracted with ethyl ether. The residue obtained is purified by chromatography (eluent: 8/2 heptane/dichloromethane). The yellow oil obtained (5.1 g; yield=100%) is dissolved in 100 ml of tetrahydrofuran, and 22 ml (22 mmol) of a 1M solution of tetrabutylammonium fluoride in tetrahydrofuran are added. The medium is stirred for one hour, acidified with 1N hydrochloric acid solution and then extracted with ethyl acetate. A beige-colored solid is obtained (3.1 g; yield=89%; m.p.=85° C.).

b. Preparation of Methyl 4-(8,8-dimethyl-5-p-tolyl-7,8-dihydro-2-naphthylselanylethynyl)-2-hydroxybenzoate:

In a manner similar to that of Example 1f, by reacting 1.3 g (2 mmol) of bis[8,8-dimethyl-5-p-tolyl-7,8-dihydro-2-naphthalene] selenide with 2 ml (2 mmol) of a 1M solution of dibromine in tetrahydrofuran, 2.29 g (12 mmol) of copper iodide, 150 ml of dimethylformamide and 0.163 g (3.6 mmol) of methyl 4-ethynyl-2-hydroxybenzoate, a yellow solid is obtained (1.85 g; yield=93%; m.p.=98° C.).

c. Preparation of Methyl 4-(8,8-dimethyl-5-p-tolyl-7,8-dihydro-2-naphthylselanylethynyl)-2-methoxybenzoate:

1.2 9 (2.4 mmol) of methyl 4-(8,8-dimethyl-5-p-tolyl-7,8-dihydro-2-naphthylselanylethynyl)-2-hydroxybenzoate are dissolved in 15 ml of dimethylformamide, and 0.3 ml (4.8 mmol) of methyl iodide is then added. The reaction medium is cooled to 0° C. and 0.12 g (2.9 mmol) of sodium hydride is then added portionwise. After 30 minutes, the medium is hydrolysed with ammonium chloride solution and extracted with ethyl ether. The residue obtained is purified by chromatography (eluent: 9/1 heptane/ethyl acetate). A white solid is obtained (1.1 g; yield=91%; m.p.=88° C.).

d. Synthesis of 4-(8,8-Dimethyl-5-p-tolyl-7,8-dihydro-2-naphthylselanylethynyl)-2-methoxybenzoic acid:

0.55 g (1.1 mmol) of methyl 4-(8,8-dimethyl-5-p-tolyl-7,8-dihydro-2-naphthylselanylethynyl)-2-methoxybenzoate is dissolved in 15 ml of tetrahydrofuran and 2 drops of water. 0.26 g (6.4 mmol) of sodium hydroxide is added. The medium is stirred for 15 hours, acidified with 2N hydrochloric acid solution and then extracted with ethyl acetate. The solid obtained is purified by chromatography (eluent: 3/7 heptane/ethyl acetate). A white solid is obtained (0.53 g; yield=99%; m.p.=150° C.).

$^1$H NMR (DMSO) 1.36 (s, 6H); 2.40 (m, 5H); 3.89 (s, 3H); 6.03 (t,1H, 4.80 Hz); 6.98 (d, 1H, 8.4 Hz); 7.19 (dd, 1H, 1.6 and 8.4 Hz); 7.29-7.23 (M, 5H); 7.49 (dd, 1H, 1.6 and 8.0 Hz); 7.72 (m, 2H).

EXAMPLE 6

Synthesis of 4-(8,8-Dimethyl-5-p-tolyl-7,8-dihydro-2-naphthylselanylethynyl)-2-hydroxybenzoic acid 1.1 g (2 mmol) of methyl 4-(8,8-dimethyl-5-p-tolyl-7,8-dihydro-2-naphthylselanylethynyl)-2-hydroxybenzoate (described in Example 5b) are dissolved in 10 ml of tetrahydrofuran, and 0.96 g (24 mmol) of sodium hydroxide is then added. The reaction medium is heated at 100° C. for 14 hours, acidified with 2N hydrochloric acid solution and then extracted with ethyl ether. The residue obtained is purified by chromatography (eluent: 7/3 heptane/ethyl acetate). After recrystallization from a heptane/ethyl ether mixture, a white solid is obtained (0.65 g; yield=61%; m.p.=201° C.).

$^1$H NMR (DMSO) 1.11 (s, 6H); 2.15 (m, 5H); 5.78 (t, 1H, 4.80 Hz); 6.74 (d, 1H, 8.4 Hz); 6.87-6.83 (M, 2H); 7.04-6.98 (M, 4H); 7.24 (dd, 1H, 1.6 and 6.4 Hz); 7.46 (s, 1H); 7.59 (d, 1H, 8.4 Hz).

EXAMPLE 7

Synthesis of 4-[5-(4-Methoxyphenyl)-8,8-dimethyl-7,8-dihydro-2-naphthylselanylethynyl]benzoic acid a. Preparation of 7-Bromo-4-(4-methoxyphenyl)-1,1-dimethyl-1,2-dihydronaphthalene:

1.77 ml (14.1 mmol) of 4-bromoanisole are dissolved in 5 ml of tetrahydrofuran and added dropwise to a suspension of 0.37 g (15.3 mmol) of magnesium in 5 ml of tetrahydrofuran. Once the formation of the organomagnesium reagent is complete, the solution is diluted with 10 ml of tetrahydrofuran and then added slowly to a solution of 3 g (11.8 mmol) of 6-bromo-4,4-dimethyl-3,4-dihydro-2H-naphthalen-1-one (described in Example 1c) in 100 ml of ethyl ether. The reaction medium is stirred for 2 hours and then treated with ammonium chloride solution and extracted with ethyl acetate. The residue obtained is dissolved in 70 ml of toluene, and 0.1 g (0.52 mmol) of para-toluenesulfonic acid is added. The reaction medium is refluxed for one hour and then treated with sodium bicarbonate solution and extracted with ethyl ether. The residue obtained is purified by chromatography (eluent: 98/2 heptane/ethyl acetate). A solid is obtained (3.1 g; yield=68%; m.p.=48° C.).

b. Preparation of bis[5-(4-Methoxyphenyl)-8,8-dimethyl-7,8-dihydro-2-naphthalene] diselenide:

3.1 ml (9 mmol) of 7-bromo-4-(4-methoxyphenyl)-1,1-dimethyl-1,2-dihydronaphthalene are dissolved in 5 ml of tetrahydrofuran and added dropwise to a suspension of 0.24 g (9.9 mmol) of magnesium in 5 ml of tetrahydrofuran. Once the formation of the Grignard reagent is complete, the solution is added slowly to a suspension of 0.67 g (8.5 mmol) of selenium in 5 ml of tetrahydrofuran. The reaction medium is stirred for one hour and then treated with 30 ml of 1N hydrochloric acid solution and extracted with ethyl acetate. The residue obtained is dissolved in 15 ml of ethanol, and 0.04 g (1 mmol) of sodium hydroxide is added. The reaction medium is stirred for 15 hours, concentrated, taken up in ethyl acetate and washed with sodium bicarbonate solution. An orange-colored oil is obtained (2.7 g; yield=90%).

c. Preparation of Methyl4-[5-(4-methoxyphenyl)-8,8-dimethyl-7,8-dihydro-2-naphthylselanylethynyl]benzoate:

In a manner similar to that of Example 1f, by reacting 1.4 g (2 mmol) of bis[5-(4-methoxyphenyl)-8,8-dimethyl-7,8-dihydro-2-naphthalene] diselenide with 2 ml (2 mmol) of a 1M solution of dibromine in tetrahydrofuran, 2.28 g (12 mmol) of copper iodide, 150 ml of dimethylformamide and 0.63 g (3.6 mmol) of methyl 4-ethynylbenzoate (described in Example 1a), a solid is obtained (1.4 g; yield=69%; m.p.=117° C.).

d. Synthesis of 4-[5-(4-Methoxyphenyl)-8,8-dimethyl-7,8-dihydro-2-naphthylselanylethynyl]benzoic acid:

0.31 g (0.62 mmol) of methyl 4-[5-(4-methoxyphenyl)-8,8-dimethyl-7,8-dihydro-2-naphthylselanylethynyl]benzoate is dissolved in 10 ml of tetrahydrofuran and 2 drops of water. 0.075 g (1.86 mmol) of sodium hydroxide is added. The medium is stirred for 2 hours, acidified with 2N hydrochloric acid solution and then extracted with ethyl acetate. The solid obtained is purified by chromatography (eluent: 3/7 heptane/ethyl acetate). A white solid is obtained (0.28 g; yield=94%; m.p.=167° C.).

$^1$H NMR (CDCl$_3$) 1.35 (s, 6H); 2.35 (d, 2H, 4.4 Hz); 3.85 (s, 3H); 5.95 (t, 1H, 4.4 Hz); 6.92 (dd, 2H, 2 and 6.4 Hz); 7.02 (d, 1H, 8 Hz); 7.25 (m, 2H); 7.33 (dd, 1H, 1.6 and 8.0 Hz); 7.57-7.52 (M, 3H); 8.05 (d, 2H, 8.0 Hz).

EXAMPLE 8

Synthesis of 6-(8,8-Dimethyl-5-p-tolyl-7,8-dihydro-2-naphthylselanylethynyl)nicotinic acid a. Preparation of Ethyl 6-iodonicotinate:

112 g (450 mmol) of 6-iodonicotinic acid are dissolved in 1.3 l of dichloromethane and 40 ml (670 mmol) of ethanol. 102 g (495 mmol) of N,N'-dicyclohexylcarbodiimide and 16.5 g (1.345 mol) of dimethylaminopyridine are added. The reaction medium is stirred for one hour, filtered through Celite and concentrated. The residue obtained is taken up in heptane and filtered to give a powder (116 g; yield=93%).

b. Preparation of Ethyl 6-ethynylnicotinate:

5 g (18 mmol) of ethyl 6-iodonicotinate are dissolved in 50 ml of triethylamine. 0.34 g (1.8 mmol) of copper iodide, 1.04 g (0.9 mmol) of tetrakis(triphenylphosphine)palladium and 2.6 ml (19 mmol) of trimethylsilylacetylene are added. The medium is stirred for 2 hours, hydrolysed and then extracted with ethyl acetate. The residue obtained is purified by chromatography (eluent: 85/15 heptane/ethyl acetate). The solid obtained (3.55 g; yield=80%) is dissolved in 50 ml of tetrahydrofuran, and 17.2 ml (17 mmol) of a 1M solution of tetrabutylammonium fluoride in tetrahydrofuran are added dropwise. The medium is stirred for 2 hours, treated with ammonium chloride solution and then extracted with ethyl acetate. A solid is obtained (1.74 g; yield=71%).

c. Preparation of Ethyl 6-(8,8-dimethyl-5-p-tolyl-7,8-dihydro-2-naphthylselanylethynyl)nicotinate:

In a manner similar to that of Example 1f, by reacting 1.5 g (2.3 mmol) of bis(8,8-dimethyl-5-p-tolyl-7,8-dihydro-2- naphthalene) diselenide (described in Example 1e) with 4.2 ml (2.1 mmol) of a 1M solution of dibromine in tetrahydrofuran, 2.63 g (14 mmol) of copper iodide, 20 ml of dimethylformamide and 0.64 g (3.7 mmol) of ethyl 6-ethynylnicotinate, a yellow oil is obtained (1.4 g; yield=76%).

d. Synthesis of 6-(8,8-Dimethyl-5-p-tolyl-7,8-dihydro-2-naphthylselanylethynyl)nicotinic acid:

In a manner similar to that of Example 7d, by reacting 0.9 g (1.8 mmol) of ethyl 6-(8,8-dimethyl-5-p-tolyl-7,8-dihydro-2-naphthylselanylethynyl)nicotinate with 0.36 g (9 mmol) of sodium hydroxide, a yellow solid is obtained (0.60 g; yield=71%; m.p.=171° C.).

$^1$H NMR (DMSO) 1.24 (s, 6H); 2.24 (d, 2H, 4 Hz); 2.28 (s, 3H); 5.54 (s, 1H); 5.89 (t, 1H, 4.8 Hz); 6.84 (d, 1H, 4.8 Hz); 6.89 (m, 2H); 7.13 (m, 4H); 7.22 (dd, 1.6 Hz, 8 Hz, 1H); 7.47 (d, 1H, 1.6 Hz); 7.70 (d, 1H, 8 Hz)

EXAMPLE 9

Synthesis of 4-(8,8-Dimethyl-5-p-tolyl-7,8-dihydro-2-naphthylselanylethynyl)-2-fluorobenzoic acid a. Preparation of Methyl 4-bromo-2-fluorobenzoate:

5 g (23 mmol) of 4-bromo-2-fluorobenzoic acid are dissolved in methanol with a few drops of sulfuric acid. The reaction medium is refluxed for 20 hours, hydrolysed and extracted with ethyl acetate. A white solid is obtained (5.6 g; yield=100%).

b. Preparation of Methyl 4-ethynyl-2-fluorobenzoate:

In a manner similar to that of Example 8b, by reacting 4.9 g (21 mmol) of methyl 4-bromo-2-fluorobenzoate with 0.4 g (2.1 mmol) of copper iodide, 1.21 g (1 mmol) of tetrakis(triphenylphosphine)palladium, 3 ml (22 mmol) of trimethylsilylacetylene and 25 ml (25 mmol) of a 1M solution of tetrabutylammonium fluoride in tetrahydrofuran, a solid is obtained (1.25 g; yield=33%).

c. Preparation of Methyl 4-(8,8-dimethyl-5-p-tolyl-7,8-dihydro-2-naphthylselanylethynyl)-2-fluorobenzoate:

In a manner similar to that of Example 1f, by reacting 1.5 g (2.3 mmol) of bis(8,8-dimethyl-5-p-tolyl-7,8-dihydro-2-naphthalene) diselenide (described in Example 1e) with 4.2 ml (2.1 mmol) of a 1M solution of dibromine in tetrahydrofuran, 2.63 g (14 mmol) of copper iodide, 20 ml of dimethylformamide and 0.66 g (3.7 mmol) of methyl 4-ethynyl-2-fluorobenzoate (described in Example 8b), a solid is obtained (1.28 g; yield=69%).

d. Synthesis of 4-(8,8-Dimethyl-5-p-tolyl-7,8-dihydro-2-naphthylselanylethynyl)-2-fluorobenzoic acid:

In a manner similar to that of Example 7d, by reacting 1.28 g (2.5 mmol) of methyl 4-(8,8-dimethyl-5-p-tolyl-7,8-dihydro-2-naphthylselanylethynyl)-2-fluorobenzoate with 0.51 g (13 mmol) of sodium hydroxide, a yellow solid is obtained (0.77 g; yield=63%; m.p.=145° C.).

$^1$H NMR (CDCl$_3$) 1.35 (s, 6H); 2.35 (d, 2H, 4.8 Hz); 2.39 (s, 3H); 5.98 (t, 1H, 4.4 Hz); 7.02 (d, 1H, 8.0 Hz); 7.18-7.23 (M, 5H); 7.28-7.32 (m, 2H); 7.55 (d, 1H, 2 Hz); 7.97 (t, 1H, 7.6 Hz).

EXAMPLE 10

Synthesis of (E)-3-[4-(8,8-Dimethyl-5-p-tolyl-7,8-dihydro-2-naphthylselanyl)phenyl]acrylic acid a. Preparation of 2-(4-Iodophenyl)ethanol:

12.5 g (50.4 mmol) of 4-iodobenzoic acid are dissolved in 125 ml of tetrahydrofuran, and 112 ml (122 mmol) of a 1M solution of borane in tetrahydrofuran are then added dropwise. The reaction medium is stirred for 4 hours, acidified with 2N hydrochloric acid solution and then extracted with ethyl acetate. A white solid is obtained (11.49 g; yield=97%).

b. Preparation of 4-Iodobenzaldehyde:

11.49 g (49.1 mmol) of 2-(4-iodophenyl)ethanol are dissolved in 375 ml of dichloromethane, and 37 g (98.2 mmol) of pyridinium dichromate are then added portionwise. The reaction medium is stirred for 15 hours, filtered through silica and eluted with dichloromethane. A yellow solid is obtained (10.4 g; yield=91%).

c. Preparation of Ethyl (E)-3-(4-iodophenyl)acrylate:

2.15 g (53.8 mmol) of sodium hydride are added portionwise to a solution of 10.7 ml (53.8 mmol) of triethyl phosphonoacetate in 50 ml of tetrahydrofuran. The reaction medium is stirred for one hour and is then added to a solution of 10.4 g (44.8 mmol) of 4-iodobenzaldehyde in 40 ml of tetrahydrofuran. The medium is stirred for 15 hours and concentrated. The residue obtained is purified by chromatography (eluent: 95/5 heptane/ethyl acetate). A yellow solid is obtained (12.2 g; yield=90%).

d. Preparation of Ethyl (E)-3-[4-(8,8-dimethyl-5-p-tolyl-7,8-dihydro-2-naphthylselanyl)phenyl]acrylate:

0.265 g (0.406 mmol) of bis(8,8-dimethyl-5-p-tolyl-7,8-dihydro-2-naphthalene) diselenide (described in Example 1e) is dissolved in 10 ml of tetrahydrofuran and 2.5 ml of ethanol. 0.046 g (1.2 mol) of sodium borohydride, 0.011 g (0.02 mmol) of bis(bipyridyl)nickel dibromide and 0.245 g (0.81 mmol) of ethyl 3-(4-iodophenyl)acrylate (described above) are added. The reaction medium is stirred for 15 hours, filtered and concentrated. The residue obtained is purified by chromatography (eluent: 95/5 heptane/ethyl acetate). A yellow solid is obtained (0.11 g; yield=30%).

e. Synthesis of (E)-3-[4-(8,8-Dimethyl-5-p-tolyl-7,8-dihydro-2-naphthylselanyl)phenyl]acrylic acid:

In a manner similar to that of Example 1g, by reacting 0.11 g (0.23 mmol) of ethyl (E)-3-[4-(8,8-dimethyl-5-p-tolyl-7,8-dihydro-2-naphthylselanyl)phenyl]acrylate with 0.11 g (2.6 mmol) of lithium hydroxide hydrate, a yellow solid is obtained (0.08 g; yield=78%).

$^1$H NMR (CDCl$_3$) 1.30 (s, 6H); 2.35 (d, 2H, 4.8 Hz); 2.38 (s, 3H); 5.98 (t, 1H, 7.6 Hz); 6.40 (d, 1H, 25.6 Hz); 7.00 (d, 1H, 12.8 Hz); 7.28-7.16 (M, 5H); 7.42-7.35 (M, 4H); 7.54 (s, 1H); 7.71 (d, 1H, 25.6 Hz).

EXAMPLE 11

Synthesis of (Z)-3-[3-(8,8-Dimethyl-5-p-tolyl-7,8-dihydro-2-naphthylselanyl)phenyl]acrylic acid a. 2-(3-Iodophenyl)ethanol:

In a manner similar to that of Example 10a, by reacting 12.5 g (50.4 mmol) of 3-iodobenzoic acid with 112 ml (122 mmol) of a 1M solution of borane in tetrahydrofuran, a yellow oil is obtained (10.22 g; yield=87%).

b. Preparation of 3-Iodobenzaldehyde:

In a manner similar to that of Example 10b, by reacting 10.22 g (43.6 mmol) of 2-(3-iodophenyl)ethanol with 32.8 g (87.2 mmol) of pyridinium dichromate, a yellow solid is obtained (9.3 g; yield=91%).

c. Preparation of Ethyl (E)-3-(3-iodophenyl)acrylate:

In a manner similar to that of Example 10c, by reacting 1.92 g (48 mmol) of sodium hydride with 9.5 ml (48 mmol) of triethyl phosphonoacetate and 9.3 g (40 mmol) of 3-iodobenzaldehyde, a yellow solid is obtained (12.2 g; yield=90%).

d. Preparation of Ethyl (E)-3-[3-(8,8-dimethyl-5-p-tolyl-7,8-dihydro-2-naphthylselanyl)phenyl]acrylate:

In a manner similar to that of Example 10d, by reacting 0.265 g (0.406 mmol) of bis(8,8-dimethyl-5-p-tolyl-7,8-dihydro-2-naphthalene) diselenide (described in Example 1e) with 0.046 g (1.2 mol) of sodium borohydride, 0.011 g (0.02 mmol) of bis(bipyridyl)nickel dibromide and 0.245 g (0.81 mmol) of ethyl (E)-3-(3-iodophenyl)acrylate (described above), a yellow solid is obtained (0.88 g; yield=22%).

e. Synthesis of (E)-3-[3-(8,8-Dimethyl-5-p-tolyl-7,8-dihydro-2-naphthylselanyl)phenyl]acrylic acid:

In a manner similar to that of Example 1g, by reacting 0.088 g (0.18 mmol) of ethyl (E)-3-[3-(8,8-dimethyl-5-p-tolyl-7,8-dihydro-2-naphthylselanyl)phenyl]acrylate with 0.09 g (2.14 mmol) of lithium hydroxide hydrate, a yellow solid is obtained (0.06 g; yield=73%).

$^1$H NMR (CDCl$_3$) 1.28 (s, 6H); 2.35 (d, 2H, 4.4 Hz); 2.38 (s, 3H); 5.97 (t, 1H, 7.6 Hz); 6.39 (d, 1H, 25.6 Hz); 6.96 (d, 1H, 12.8 Hz); 7.50-7.14 (M, 9H); 7.61 (s, 1H); 7.69 (d, 1H, 25.6 Hz).

EXAMPLE 12

Synthesis of 3-{4-[5-(4-tert-Butylphenyl)-8,8-dimethyl-7,8-dihydro-2-naphthylselanyl]phenyl}acrylic acid a. Preparation of Ethyl 3-(4-[5-(4-tert-butylphenyl)-8,8-dimethyl-7,8-dihydro-2-naphthylselanyliphenyl]acrylate:

In a manner similar to that of Example 10e, by reacting 0.039 g (0.053 mmol) of bis[5-(4-tert-butylphenyl)-8,8-dimethyl-7,8-dihydro-2-naphthalene] diselenide (described in Example 3b) with 0.007 g (0.16 mmol) of sodium borohydride, 0.005 g (0.009 mol) of bis(bipyridyl)nickel dibromide and 0.02 g (0.07 mmol) of ethyl (E)-3-(4-iodophenyl)acrylate (described in Example 10c), a yellow oil is obtained.

b. Synthesis of 3-(4-[5-(4-tert-Butylphenyl)-8,8-dimethyl-7,8-dihydro-2-naphthylselanyl]phenyl)acrylic acid:

In a manner similar to that of Example 1g, a saponification is performed on the above product.

$^1$H NMR (CDCl$_3$) 1.30 (s, 15H); 2.35 (d, 2H, 4.8 Hz); 5.98 (t, 1H, 7.6 Hz); 6.40 (d, 1H, 25.6 Hz); 7.00 (d, 1H, 12.8 Hz); 7.28-7.16 (M, 5H); 7.42-7.35 (M, 4H); 7.54 (s, 1H); 7.71 (d, 1H, 25.6 Hz).

EXAMPLE 13

Synthesis of 3-{3-[5-(4-tert-Butylphenyl)-8,8-dimethyl-7,8-dihydro-2-naphthylselanyl]phenyl}acrylic acid a. Preparation of Ethyl 3-(3-[5-(4-tert-butylphenyl)-8,8-dimethyl-7,8-dihydro-2-naphthylselanyl]phenyl)acrylate:

In a manner analogous to Example 10d, by reacting 0.039 g (0.053 mmol) of bis[5-(4-tert-butylphenyl)-8,8-dimethyl-7,8-dihydro-2-naphthalene] diselenide (described in Example 3b) with 0.007 g (0.16 mmol) of sodium borohydride, 0.005 g (0.009 mmol) of bis(bipyridyl)nickel dibromide and 0.02 g (0.07 mmol) of ethyl (E)-3-(3-iodophenyl)acrylate (described in Example 11c), a yellow oil is obtained.

b. Synthesis of 3-(3-[5-(4-tert-Butylphenyl)-8,8-dimethyl-7,8-dihydro-2-naphthylselanyl]phenyl{acrylic acid:

In a manner similar to that of Example 1g, a saponification is performed on the above product.

$^1$H NMR (CDCl$_3$) 1.28 (s, 15H); 2.35 (d, 2H, 4.4 Hz); 5.97 (t, 1H, 7.6 Hz); 6.39 (d, 1H, 25.6 Hz); 6.96 (d, 1H, 12.8 Hz); 7.50-7.14 (M, 9H); 7.61 (s, 1H); 7.69 (d, 1H, 25.6 Hz).

EXAMPLE 14

Synthesis of 6-(8,8-Dimethyl-5-p-tolyl-7,8-dihydro-2-naphthylselanyl)naphthalene-2-carboxylic acid a. Preparation of 2-(6-Bromo-2-naphthyl)-4,4-dimethyl-4,5-dihydrooxazole:

11 g (43.8 mmol) of 6-bromo-2-naphthoic acid are dissolved in 300 ml of dichloromethane and 5 ml of pyridine. The medium is cooled to 0° C. and 4.7 ml of thionyl chloride are added dropwise, and the medium is then stirred for 2 hours while allowing the temperature to rise. After concentrating, the residue is dissolved in 150 ml of toluene and 27.3 g (307 mmol) of 2-amino-2-methyl-1-propanol are added. The medium is heated at 50° C. for 4 hours, treated with 1N hydrochloric acid solution and extracted with ethyl acetate. The residue obtained is dissolved in dichloromethane and the medium is cooled to 0° C. 3.8 ml of thionyl chloride are added dropwise and the medium is stirred for 6 hours and then hydrolysed and extracted with dichloromethane. The residue obtained is purified by chromatography (eluent: 90/10 heptane/ethyl acetate). A solid is obtained (8.1 g; yield=61%).

b. Preparation of 1,1-Dimethyl-7-selenocyanato-4-p-tolyl-1,2-dihydronaphthalene:

3.2 g (4.9 mmol) of bis[8,8-dimethyl-5-p-tolyl-7,8-dihydro-2-naphthalene] selenide (described in Example 1e) are dissolved in 100 ml of tetrahydrofuran at −78° C., and 4.9 ml (4.9 mmol) of a 1M solution of dibromine in tetrahydrofuran are then added dropwise. After 30 minutes, the reaction medium is added dropwise to a solution of 1.6 ml (12 mmol) of trimethylsilyl cyanide in 40 ml of tetrahydrofuran at room temperature. After 30 minutes, the medium is concentrated to dryness.

c. Preparation of 2-[6-(8,8-Dimethyl-5-p-tolyl-7,8-dihydro-2-naphthylselanyl)naphthalen-2-yl]-4,4-dimethyl-4,5-dihydrooxazole:

1.52 g (5 mmol) of 2-(6-bromo-2-naphthyl)4,4-dimethyl4,5-dihydrooxazole are dissolved in 50 ml of tetrahydrofuran at −78° C., and 2.1 ml (5.25 mmol) of 2.5M butyllithium are then added dropwise. After 30 minutes, the reaction medium is added dropwise to a solution of 1.94 g (5.5 mmol) of 1,1-dimethyl-7-selenocyanato4-p-tolyl-1,2-dihydro-naphthalene dissolved in tetrahydrofuran at −78° C. The medium is warmed to 0° C., stirred for 2 hours treated with ammonium chloride solution and extracted with ethyl acetate. The residue obtained is purified by chromatography (eluent: 90/10 heptane/ethyl acetate). A solid is obtained (2.75 g; yield=70%).

d. Synthesis of 6-(8,8-Dimethyl-5-p-tolyl-7,8-dihydro-2-naphthylselanyl)-2-naphthalenecarboxylic acid:

1 g (1.81 mmol) of 2-[6-(8,8-dimethyl-5-p-tolyl-7,8-dihydro-2-naphthylselanyl)naphthalen-2-yl]-4,4-dimethyl-4,5-dihydrooxazole is dissolved in 10 ml of tetrahydrofuran, and 15 ml of 5N hydrochloric acid solution are then added. The reaction medium is refluxed for 4 hours with stirring, hydrolysed and extracted with ethyl ether. The residue obtained is purified by chromatography (eluent: 4/6-heptane/ethyl acetate). A solid is obtained (0.55 g; yield=61%; 207° C.).

$^1$H NMR (CDCl$_3$) 1.30 (s, 6H); 2.37 (d, 2H, 4.8 Hz); 2.38 (s, 3H); 5.99 (t, 1H, 7.6 Hz); 7.00 (d, 1H, 8 Hz); 7.29-7.18 (M, 5H); 7.52 (dd, 1H, 1.6 and 8.4 Hz); 7.58 (d, 1H, 2 Hz);

7.75 (d, 1H, 8.4 Hz); 7.82 (d, 1H, 8.4 Hz); 7.89 (s, 1H); 8.05 (dd, 1H, 1.6 and 8.4 Hz); 8.60 (s, 1H).

EXAMPLE 15

Synthesis of 4-[3-(8,8-Dimethyl-5-p-tolyl-7,8-dihydro-2-naphthyl)-3-hydroxyprop-1-ynyl]benzoic acid a. Preparation of 8,8-Dimethyl-5-p-tolyl-7,8-dihydro-2-naphthalenecarbaldehyde:

53.3 g (162 mmol) of 7-bromo-1,1-dimethyl-4-p-tolyl-1,2-dihydro-naphthalene (described in Example 1d) are dissolved in 320 ml of tetrahydrofuran at −65° C., and 72 ml (180 mmol) of 2.5M butyllithium are then added dropwise. After one hour, 14 ml (180 mmol) of dimethylformamide are added dropwise while maintaining the temperature at −65° C. The reaction medium is stirred for 2 hours while allowing the temperature to rise, and the medium is then hydrolysed and extracted with toluene. The residue obtained is purified by chromatography (eluent: 95/5 heptane/ethyl acetate). A yellow solid is obtained (27 g; yield=60%).

b. Preparation of 1-(8,8-Dimethyl-5-p-tolyl-7,8-dihydro-2-naphthyl)-3-trimethylsilanylpropynone:

8 ml (19.9 mmol) of 2.5M butyllithium are added dropwise to 2.8 ml (19.9 mmol) of trimethylsilylacetylene dissolved in 10 ml of tetrahydrofuran at −78° C. After 2 hours, the reaction medium is added dropwise to 5 g (18.1 mmol) of 8,8-dimethyl-5-p-tolyl-7,8-dihydro-2-naphthalenecarbaldehyde dissolved in 20 ml of tetrahydrofuran. The reaction medium is stirred for 2 hours while allowing the temperature to rise, and the medium is then treated with 2N hydrochloric acid solution and extracted with ethyl ether. The residue obtained is purified by chromatography (eluent: 95/5 heptane/ethyl acetate). A yellow oil is obtained (6.1 g; yield=90%).

c. Preparation of 1-(8,8-Dimethyl-5-p-tolyl-7,8-dihydro-2-naphthyl)propynone:

6.1 g (16.3 mmol) of 1-(8,8-dimethyl-5-p-tolyl-7,8-dihydro-2-naphthyl)-3-trimethylsilanylpropynone and 4.73 g (32.6 mmol) of potassium fluoride on alumina (40%) are dissolved in 35 ml of tetrahydrofuran, 35 ml of ethanol and 3.5 ml of water. The reaction medium is stirred for two hours, treated with 1N hydrochloric acid solution and extracted with ethyl acetate. The residue obtained is purified by chromatography (eluent: 95/5 heptane/ethyl acetate). A yellow oil is obtained (4.6 g; yield=93%).

d. Synthesis of 4-[3-(8,8-Dimethyl-5-p-tolyl-7,8-dihydro-2-naphthyl)-3-hydroxyprop-1-ynyl]benzoic acid:

1.5 g (5 mmol) of 1-(8,8-dimethyl-5-p-tolyl-7,8-dihydro-2-naphthyl)-propynone and 0.831 g (3.35 mmol) of 4-iodobenzoic acid are dissolved in 15 ml of tetrahydrofuran and 15 ml of triethylamine. The medium is degassed with nitrogen and then 0.065 g (0.084 mmol) of trans-dichlorobis(triphenylphosphine)palladium and 0.045 g (0.218 mmol) of copper iodide are then added. After 3 hours, the medium is treated with 1N hydrochloric acid solution and extracted with ethyl ether. The residue obtained is purified by chromatography (eluent: 7/3 heptane/ethyl acetate). A yellow solid is obtained (1.2 g; yield=86%; 111° C.).

$^1$H NMR (CDCl$_3$) 1.36 (s, 6H); 2.35 (d, 2H, 8.4 Hz); 2.39 (s, 3H); 5.70 (s, 1H); 5.98 (m, 1H); 7.09 (d, 8 Hz); 7.27-7.18 (M, 4H); 7.35-7.33 (M, 1H); 7.68-7.52 (M, 3H); 8.04 (d, 2H, 8 Hz).

EXAMPLE 16

Synthesis of 4-[3-(8,8-Dimethyl-5-p-tolyl-7,8-dihydro-2-naphthyl)-3-hydroxyprop-1-ynyl]-2-hydroxybenzoic acid a. Preparation of 1-(8,8-Dimethyl-5-p-tolyl-7,8-dihydro-2-naphthyl)propynone:

6.66 g (24 mmol) of 8,8-dimethyl-5-p-tolyl-7,8-dihydro-2-naphthenecarbaldehyde (described in Example 15a) are dissolved in 100 ml of tetrahydrofuran at 0° C., and 62 ml (31 mmol) of a 0.5M solution of ethynylmagnesium bromide in tetrahydrofuran are then added dropwise. After 2 hours, the medium is treated with ammonium chloride solution and extracted with ethyl acetate. The residue obtained is purified by chromatography (eluent: 85/15 heptane/ethyl acetate). A yellow oil is obtained (1.2 g; yield=86%).

b. Synthesis of 4-[3-(8,8-Dimethyl-5-p-tolyl-7,8-dihydro-2-naphthyl)-3-hydroxyprop-1-ynyl]-2-hydroxybenzoic acid:

In a manner similar to that of Example 15d, with 0.6 g (2 mmol) of 1-(8,8-dimethyl-5-p-tolyl-7,8-dihydro-2-naphthyl)propynone, 0.449 g (1.7 mmol) of 2-hydroxy-4-iodobenzoic acid, 0.03 g (0.042 mmol) of trans-dichlorobis(triphenylphosphine)palladium and 0.016 g (0.085 mmol) of copper iodide, a brown oil is obtained (0.418 g; yield=56%; 228° C.).

$^1$H NMR (DMSO) 1.24 (s, 6H); 2.24 (d, 2H, 4 Hz); 2.28 (s, 3H); 5.54 (s, 1H); 5.89 (t, 1H, 4.8 Hz); 6.84 (d, 1H, 4.8 Hz); 6.89 (m, 2H); 7.13 (m, 4H); 7.22 (dd, 1.6 Hz, 8 Hz, 1H); 7.47 (d, 1H), 1.6 Hz); 7.70 (d, 1H, 8 Hz)

EXAMPLE 17

Synthesis of 4-3-[5-(4-Ethoxymethoxyphenyl)-8,8-dimethyl-7,8-dihydro-2-naphthyl]-3-hydroxyprop-1-ynyl}benzoic acid a. Preparation of 1-Bromo-4-ethoxymethoxybenzene:

20 g (116 mmol) of 4-bromophenol dissolved in 20 ml of dimethylformamide are added dropwise to a suspension of 5.6 g (139 mmol) of sodium hydride in 200 ml of dimethylformamide at 0° C. After 40 minutes, 12.9 ml (139 mmol) of chloromethoxyethane are added dropwise. The medium is warmed to room temperature, stirred for 15 hours, hydrolysed and extracted with ethyl acetate. An oil is obtained (27 g; yield=100%).

b. Preparation of 4-(6-Bromo-4,4-dimethyl-3,4-dihydro-1-naphthyl)phenol:

23.27 g (100 mmol) of 1-bromo-4-ethoxymethoxybenzene dissolved in 50 ml of tetrahydrofuran are added dropwise to 3.14 g (130 mmol) of magnesium suspended in 50 ml of tetrahydrofuran. After 15 minutes, the solution obtained is added to a solution of 21 g (83 mmol) of 6-bromo-4,4-dimethyl-3,4-dihydro-2H-naphthalen-1-one (described in Example 1c) in 150 ml of ethyl ether at 0° C. After 3 hours, the medium is treated with ammonium chloride solution and extracted with ethyl ether. The yellow oil obtained is dissolved in 150 ml of toluene, and 0.713 g (3.75 mmol) of para-toluenesulfonic acid is then added. The reaction medium is refluxed for one hour and, after cooling, 200 ml of methanol and a few drops of sulfuric acid are then added. The medium is stirred for 15 hours, treated with sodium bicarbonate solution and extracted with ethyl ether.

The residue obtained is purified by chromatography (eluent: 90/10 heptane/ethyl acetate). An oil is obtained (19.2 g; yield=70%).

c. Preparation of 7-Bromo-4-(4-ethoxymethoxyphenyl)-1,1-dimethyl-1,2-dihydronaphthalene:

In a manner similar to that of Example 17a, by reacting 15 g (46 mmol) of 4-(6-bromo-4,4-dimethyl-3,4-dihydro-1-naphthyl)phenol with 2.2 g (55 mmol) of sodium hydride and 5.1 ml (55 mmol) of chloromethoxyethane, an oil is obtained (11 g; yield=62%).

d. Preparation of 5-(4-Ethoxymethoxyphenyl)-8,8-dimethyl-7,8-dihydro-2-naphthalenecarbaldehyde:

In a manner similar to that of Example 15a, by reacting 11 g (28 mmol) of 7-bromo-4-(4-ethoxymethoxyphenyl)-1,1-dimethyl-1,2-dihydronaphthalene with 17 ml (43 mmol) of 2.5M butyllithium and 3.34 ml (43 mmol) of dimethylformamide, a yellow oil is obtained (2.7 g; yield=29%).

e. Preparation of 1-[5-(4-Ethoxymethoxyphenyl)-8,8-dimethyl-7,8-dihydro-2-naphthyl]propynone:

In a manner similar to that of Example 16a, by reacting 0.5 g (1.5 mmol) of 5-(4-ethoxymethoxyphenyl)-8,8-dimethyl-7,8-dihydro-2-naphthalenecarbaldehyde with 3.9 ml (1.9 mmol) of a 0.5M solution of ethynylmagnesium bromide in tetrahydrofuran, a yellow oil is obtained (0.44 g; yield=81%).

f. Synthesis of 4-{3-[5-(4-Ethoxymethoxyphenyl)-8,8-dimethyl-7,8-dihydro-2-naphthyl]-3-hydroxyprop-1-ynyl}benzoic acid:

In a manner similar to that of Example 16b, by reacting 0.44 g (1.2 mmol) of 1-[5-(4-ethoxymethoxyphenyl)-8,8-dimethyl-7,8-dihydro-2-naphthyl]propynone with 0.248 g (1 mmol) of 4-iodobenzoic acid, 0.021 g (0.03 mmol) of trans-dichlorobis(triphenylphosphine)palladium and 0.011 g (0.006 mmol) of copper iodide, a yellow solid is obtained (0.352 g; yield=61%; 89° C.).

$^1$H NMR (CDCl$_3$) 1.29 (s, 3H); 1.38 (s, 6H); 2.37 (d, 2H, 4.8 Hz); 3.79 (q, 2H, 6.8 Hz); 5.28 (s, 2H); 5.72 (s, 1 Hz); 5.99 (t, 1H, 4.8 Hz), 7.08 (dd, 2H, 2.4 and 6.8 Hz); 7.12 (d, 1H, 8 Hz); 7.29-7.26 (M, 2H); 7.37 (dd, 1H, 1.6H and 8 Hz); 7.57 (d, 1H, 8.4 Hz); 7.61 (d, 2H, 1.6 Hz); 8.07 (d, 2H, 7.4 Hz).

EXAMPLE 18

Synthesis of 4-{3-[5-(4-Benzyloxyphenyl)-8,8-dimethyl-7,8-dihydro-2-naphthyl]-3-hydroxyprop-1-ynyl}benzoic acid a. Preparation of 1-[5-(4-Ethoxymethoxyphenyl)-8,8-dimethyl-7,8-dihydro-2-naphthyl]propynone:

2.18 g (6.5 mmol) of 5-(4-ethoxymethoxyphenyl)-8,8-dimethyl-7,8-dihydro-2-naphthalenecarbaldehyde (described in Example 17d) are dissolved in 20 ml of methanol and a few drops of sulfuric acid are added. After stirring for two hours at room temperature, the reaction medium is hydrolysed and extracted with ethyl acetate. The residue obtained is purified by chromatography (eluent: 85/15 heptane/ethyl acetate). A white solid is obtained (1.2 g; yield=66%).

b. Preparation of 5-(4-Benzyloxyphenyl)-8,8-dimethyl-7,8-dihydro-2-naphthalenecarbaldehyde:

In a manner similar to that of Example 17a, by reacting 0.3 g (1.1 mmol) of 1-[5-(4-ethoxymethoxyphenyl)-8,8-dimethyl-7,8-dihydro-2-naphthyl]propynone with 0.052 g (1.3 mmol) of sodium hydride and 0.14 ml (1.2 mmol) of benzyl bromide, an oil is obtained (0.29 g; yield=73%).

c. Preparation of 1-[5-(4-Benzyloxyphenyl)-8,8-dimethyl-7,8-dihydro-2-naphthyl]prop-2-yn-1-ol:

In a manner similar to that of Example 16a, by reacting 0.29 g (0.79 mmol) of 5-(4-benzyloxyphenyl)-8,8-dimethyl-7,8-dihydro-2-naphthalene-carbaldehyde with 2 ml (1 mmol) of a 0.5M solution of ethynylmagnesium bromide in tetrahydrofuran, a colorless oil is obtained (0.28 g; yield=90%).

d. Synthesis of 4-{3-[5-(4-Benzyloxyphenyl)-8,8-dimethyl-7,8-dihydro-2-naphthyl]-3-hydroxyprop-1-ynyl}benzoic acid:

In a manner similar to that of Example 16b, by reacting 0.28 g (0.71 mmol) of 1-[5-(4-benzyloxyphenyl)-8,8-dimethyl-7,8-dihydro-2-naphthyl]prop-2-yn-1-ol with 0.146 g (0.6 mmol) of 4-iodobenzoic acid, 0.010 g (0.015 mmol) of trans-dichlorobis(triphenylphosphine)palladium and 0.006 g (0.003 mmol) of copper iodide, a yellow solid is obtained (0.03 g; yield=10%; m.p.=171° C.).

$^1$H NMR (DMSO) 1.30 (s, 6H); 2.30 (d, 2H, 4 Hz); 5.14 (s, 2H); 5.62 (d. 1H, 5.2 Hz); 5.75 (m, 1H); 6.20 (d, 1Hz, 5.6 Hz); 6.93 (d, 1H, 8.0 Hz); 7.04 (d, 2H, 8.0 Hz); 7.22 (d, 2H, 8.0 Hz); 7.30 (d, 2H, 8.0 Hz); 7.35 (d, 2H, 8.0 Hz); 7.41 (t, 2H, 8.0 Hz); 7.47 (d, 2H, 8.0 Hz); 7.55 (d, 3H, 1.6 Hz); 7.92 (d, 2H, 8.0 Hz).

EXAMPLE 19

Synthesis of 4-{3-[5-(4-Dimethylaminophenyl)-8,8-dimethyl-7,8-dihydro-2-naphthyl]-3-hydroxyprop-1-ynyl}benzoic acid a. Preparation of [4-(6-Bromo-4,4-dimethyl-3,4-dihydro-1-naphthyl)phenyl]dimethylamine:

In a manner similar to that of Example 7a, by reacting 19 g (95 mmol) of 4-bromoaniline with 2.5 g (104 mmol) of magnesium, 20 g (79 mmol) of 6-bromo-4,4-dimethyl-3,4-dihydro-2H-naphthalen-1-one (described in Example 1c) and 0.677 g (3.56 mmol) of para-toluenesulfonic acid, a solid is obtained (21.6 g; yield=77%; m.p.=104° C.).

b. Preparation of 5-(4-Dimethylaminophenyl)-8,8-dimethyl-7,8-dihydro-2-naphthalenecarbaldehyde:

In a manner similar to that of Example 15a, by reacting 16 g (45 mmol) of [4-(6-bromo-4,4-dimethyl-3,4-dihydro-1-naphthyl)-phenyl]dimethylamine with 27 ml (67 mmol) of 2.5M butyllithium and 5.2 ml (67 mmol) of dimethylformamide, a yellow solid is obtained (7 g; yield=50%; m.p.=108° C.).

c. Preparation of 1-[5-(4-Dimethylaminophenyl)-8,8-dimethyl-7,8-dihydro-2-naphthyl]prop-2-yn-1-ol:

In a manner similar to that of Example 16a, by reacting 1 g (3.3 mmol) of 5-(4-dimethylaminophenyl)-8,8-dimethyl-7,8-dihydro-2-naphthalenecarbaldehyde with 8.5 ml (4.2 mmol) of a 0.5M solution of ethynylmagnesium bromide in tetrahydrofuran, a colorless oil is obtained (0.81 g; yield=74%).

d. Synthesis of 4-{3-[5-(4-Dimethylaminophenyl)-8,8-dimethyl-7,8-dihydro-2-naphthyl-2-yl]-3-hydroxyprop-1-ynyl}benzoic acid:

In a manner similar to that of Example 16b, by reacting 0.81 g (2.4 mmol) of 1-[5-(4-dimethylaminophenyl)-8,8-dimethyl-7,8-dihydro-2-naphthyl]prop-2-yn-1-ol with 0.496 g (2 mmol) of 4-iodobenzoic acid, 0.035 g (0.05 mmol) of trans-dichlorobis(triphenylphosphine)palladium and 0.019 g (b.1 mmol) of copper iodide, a beige-colored solid is obtained (0.65 g; yield=72%; m.p.=91° C.).

$^1$H NMR (CDCl$_3$) 1.38 (s, 6H); 2.35 (d, 2H, 4.8 Hz); 3.00 (s, 6H); 5.72 (s, 1H); 5.97 (t, 1H, 4.8 Hz); 6.80 (d, 2H, 8 Hz);

7.19 (d, 1H, 8 Hz); 7.26 (m, 2H); 7.37 (dd, 1H, 4.0 and 8.0 Hz); 7.59 (m, 3H); 8.07 (d, 2H, 8.0 Hz).

EXAMPLE 20

Synthesis of 4-[3-(8,8-Dimethyl-5-p-tolyl-7,8-dihydro-2-naphthyl)-3-oxoprop-1-ynyl]benzoic acid 0.1 g (0.237 mmol) of 4-[3-(8,8-dimethyl-5-p-tolyl-7,8-dihydro-2-naphthyl)-3-hydroxyprop-1-ynyl]benzoic acid (described in Example 15d) is dissolved in 2 ml of pentane and 2 ml of dichloromethane, 0.31 g (3.55 mmol) of manganese dioxide is then added and the medium is heated at 37° C. for 24 hours. The medium is filtered and concentrated, and the residue obtained is purified by chromatography (eluent: 85/15 heptane/ethyl acetate). A white solid is obtained (0.02 g; yield=20%).

$^1$H NMR (CDCl$_3$) 1.36 (s, 6H); 2.35 (d, 2H, 8.4 Hz); 2.39 (s, 3H); 5.98 (m, 1H); 7.09 (d, 8 Hz); 7.27-7.18 (M, 4H); 7.35-7.33 (M, 1H); 7.68-7.52 (M, 3H); 8.04 (d, 2H, 8 Hz).

EXAMPLE 21

Synthesis of 4-[3-(8,8-Dimethyl-5-p-tolyl-7,8-dihydro-2-naphthyl)-3-hydroxypropenyl]benzoic acid a. Preparation of 1-(8,8-Dimethyl-5-p-tolyl-7,8-dihydro-2-naphthyl)ethanone:

5 g (18.1 mmol) of 8,8-dimethyl-5-p-tolyl-7,8-dihydro-2-naphthalenecarbaldehyde (described in Example 15a) are dissolved in tetrahydrofuran at 0° C., and 7.2 ml (21.7 mmol) of methylmagnesium bromide are then added. The medium is stirred for 1 hour while allowing the temperature to rise, and is then treated with ammonium chloride solution, extracted with ethyl ether and filtered through silica. The residue obtained is dissolved in dichloromethane and 15.7 g (181 mmol) of manganese dioxide are added. The medium is heated at 50° C. for 15 hours, filtered and concentrated, and the residue obtained is purified by chromatography (eluent: 85/15 heptane/ethyl acetate). A solid is obtained (5 g; yield=96%).

b. Preparation of 4-[3-(8,8-Dimethyl-5-p-tolyl-7,8-dihydro-2-naphthyl)-3-oxopropenyl]benzoic acid:

5 g (17.2 mmol) of 1-(8,8-dimethyl-5-p-tolyl-7,8-dihydro-2-naphthyl)-ethanone are dissolved in 150 ml of methanol, and 2.86 g (17.2 mmol) of methyl 4-formylbenzoate and 100 ml of 1N sodium hydroxide are then added. The reaction medium is stirred for 13 hours, concentrated, treated with concentrated hydrochloric acid and extracted with ethyl ether. The residue obtained is purified by chromatography (eluent: 4/6 heptane/ethyl acetate). A solid is obtained (3.5 g; yield=46%; m.p.=245° C.).

c. Synthesis of 4-[3-(8,8-Dimethyl-5-p-tolyl-7,8-dihydro-2-naphthyl)-3-hydroxypropenyl]benzoic acid:

2 g (4.7 mmol) of 4-[3-(8,8-dimethyl-5-p-tolyl-7,8-dihydro-2-naphthyl)-3-oxopropenyl]benzoic acid are dissolved in 50 ml of methanol, and 2.1 g (5.6 mmol) of caesium chloride are then added. After 30 minutes, 0.18 g (4.8 mmol) of sodium borohydride is added. After 30 minutes, the medium is treated with ammonium chloride solution and extracted with ethyl acetate. The residue obtained is purified by chromatography (eluent: 50/50 heptane/ethyl acetate). A solid is obtained (0.42 g; yield=21%; m.p.>300° C., dec).

$^1$H NMR (DMSO) 1.26 (s, 6H); 2.25 (m, 2H); 2.28 (s, 3H); 5.26 (d, 1H, 6.7 Hz); 5.66 (d, 1H, 5.9 Hz); 5.87 (m, 1H); 6.61 (m, 1H); 6.84 (m, 2H); 7.15 (m, 6H); 7.44 (m, 1); 7.74 (m, 2H).

EXAMPLE 22

Synthesis of 6-[(8,8-Dimethyl-5-p-tolyl-7,8-dihydro-2-naphthyl)hydroxymethyl]-2-naphthalenecarboxylic acid a. Preparation of Monomethyl ester of 2,6-naphthalenedicarboxylic acid:

49 g (200 mmol) of dimethyl 2,6-naphthalenedicarboxylate and 42.2 g (1 mol) of lithium hydroxide monohydrate are dissolved in 750 ml of tetrahydrofuran. The medium is refluxed for 26 hours, concentrated to dryness, triturated from 2 liters of 2N hydrochloric acid, filtered and washed until neutral. A solid is obtained (43 g; yield=94%; m.p.=265° C.).

b. Preparation of Methyl 6-formyl-2-naphthalenecarboxylate:

5.5 g (24 mmol) of the monomethyl ester of 2,6-naphthalenedicarboxylic acid are dissolved in tetrahydrofuran and 36 ml (36 mmol) of a 1M solution of borane in tetrahydrofuran are then added dropwise. The medium is stirred for 15 hours, hydrolysed with ice and extracted with ethyl acetate. The white solid obtained is dissolved in dichloromethane and 20 g (230 mmol) of manganese dioxide are then added. The medium is stirred for 15 hours and filtered. The residue obtained is recrystallized from an ethyl acetate/heptane mixture. A white solid is obtained (3.9 g; yield=68%; m.p.=125° C.).

c. Preparation of Methyl 6-chlorocarbonyl-2-naphthalenecarboxylate:

3.9 g (16.8 mmol) of methyl 6-formyl-2-naphthalenecarboxylate are dissolved in 70 ml of thionyl chloride and the medium is then refluxed for two hours and concentrated to dryness.

d. Preparation of Methyl 6-(8,8-dimethyl-5-p-tolyl-7,8-dihydro-2-naphthylcarbonyl)-2-naphthalenecarboxylate:

5 g (15.3 mmol) of 7-bromo-1,1-dimethyl-4-p-tolyl-1,2-dihydro-naphthalene (described in Example 1d) are dissolved in tetrahydrofuran and 9.5 ml (16 mmol) of 1.7M tert-butyllithium are then added. After 15 minutes, 16 ml (16 mmol) of a 1M solution of zinc chloride are added, followed, after 30 minutes, by the addition of the methyl 6-chlorocarbonyl-2-naphthalene-carboxylate prepared above and 0.88 g (0.765 mmol) of tetrakis(triphenylphosphine)palladium. The medium is refluxed for 24 hours, treated with ammonium chloride solution and extracted with ethyl acetate. The residue obtained is purified by chromatography (eluent: heptane). A solid is obtained (4.8 g; yield=38%).

e. Preparation of Methyl 6-[(8,8-dimethyl-5-p-tolyl-7,8-dihydro-2-naphthyl)hydroxymethyl]-2-naphthalenecarboxylate:

0.7 g (1.52 mmol) of methyl 6-(8,8-dimethyl-5-p-tolyl-7,8-dihydro-2-naphthylcarbonyl)-2-naphthalenecarboxylate is dissolved in methanol at 0° C. and 0.115 g (3 mmol) of sodium borohydride is then added. The medium is stirred for 2 hours, treated with ammonium chloride solution and extracted with ethyl ether. The residue obtained is purified by chromatography. A solid is obtained (0.7 g; yield=100%).

f. Synthesis of 6-[(8,8-Dimethyl-5-p-tolyl-7,8-dihydro-2-naphthyl)hydroxymethyl)]-2-naphthalenecarboxylic acid:

0.5 g (1.08 mmol) of methyl 6-(8,8-dimethyl-5-p-tolyl-7,8-dihydro-2-naphthylcarbonyl)-2-naphthalenecarboxylate is dissolved in 15 ml of tetrahydrofuran, 15 ml of water and 5 ml of methanol, and 0.14 g (3.25 mmol) of lithium hydroxide monohydrate is then added. The medium is refluxed for 2 hours, treated with 1N hydrochloric acid solution and extracted with ethyl acetate. The residue obtained is recrystallized from an ethyl acetate/heptane mixture. A white solid is obtained (0.45 g; yield=94%; 110° C.).

$^1$H NMR (DMSO) 1.06 (s, 6H); 2.07 (d, 2H, 4.4 Hz); 2.12 (s, 3H); 5.70 (m, 2H); 6.63 (d, 1H, 8.0 Hz); 6.96 (m, 4H); 7.31 (s, 1H); 7.39 (d, 2H, 8.4 Hz); 7.84-7.74 (M, 5H); 8.34 (s, 1H).

EXAMPLE 23

Synthesis of 6-(8,8-Dimethyl-5-p-tolyl-7,8-dihydro-2-naphthylcarbonyl)-2-naphthalenecarboxylic acid In a manner similar to that of Example 22e, by reacting 0.5 g (1 mmol) of methyl 6-(8,8-dimethyl-5-p-tolyl-7,8-dihydro-2-naphthylcarbonyl)-2-naphthalenecarboxylate (described in Example 22c) with 0.126 g (3 mmol) of lithium hydroxide hydrate, a solid is obtained (0.48 g; yield=98%; m.p.=267° C.).

$^1$H NMR (DMSO) 1.58 (s, 6H); 2.59 (s, 3H); 2.64 (d, 2H, 4.8 Hz); 6.40 (t, 1H, 4.8 Hz); 7.32 (d, 1H, 8.0 Hz); 7.49 (s, 4H); 7.83 (dd, 1H, 1.6 and 8 Hz); 8.10 (d, 1H, 1.6 Hz); 8.16 (dd, 1H, 1.6 and 8.4 Hz); 8.30 (dd, 1H, 1.6 and 8.6 Hz); 8.47 (d, 1H, 8.4 Hz); 8.53 (d, 1H, 8.8 Hz), 8.64 (s, 1H); 8.94 (s, 1H).

EXAMPLE 24

Synthesis of 4-[2-(8,8-Dimethyl-5-p-tolyl-7,8-dihydro-2-naphthyl)-2-oxoacetylamino]benzoic acid a. Preparation of (8,8-Dimethyl-5-p-tolyl-7,8-dihydro-2-naphthyl)oxoacetic acid:

23 g (16 mmol) of 7-bromo-1,1-dimethyl4-p-tolyl-1,2-dihydro-naphthalene (described in Example 1d) are dissolved in tetrahydrofuran at −78° C., and 7.04 ml (17.6 mmol) of 2.5M butyllithium are then added. After 30 minutes, 4.96 g (19.2 mmol) of magnesium bromide diethyl etherate are added. After 15 minutes, the medium is cannulated onto a mixture of 2.87 g (20 mmol) of copper bromide and 3.47 g (40 mmol) of lithium bromide in tetrahydrofuran at 0° C. After 10 minutes, 1.97 ml (17.6 mmol) of ethyl oxalate chloride are added dropwise. The medium is stirred for 1 hour, treated with ammonium chloride solution and extracted with ethyl ether. The residue obtained is dissolved in 50 ml of tetrahydrofuran and 1 ml of water, and 2.5 g (64 mmol) of sodium hydroxide are then added. The medium is stirred for 15 hours, treated with concentrated hydrochloric acid solution and extracted with ethyl ether. The residue obtained is purified by chromatography (eluent: 60/40 heptane/ethyl acetate). A solid is obtained (2.3 g; yield=45%).

b. Preparation of Methyl 4-[2-(8,8-dimethyl-5-p-tolyl-7,8-dihydro-2-naphthyl)-2-oxoacetylamino]benzoate:

1.2 g (3.75 mmol) of (8,8-dimethyl-5-p-tolyl-7,8-dihydro-2-naphthyl)oxoacetic acid are dissolved in dichloromethane, and 0.33 ml (3.75 mmol) of oxalyl chloride and 0.5 ml (3.75 mmol) of triethylamine are then added. The medium is stirred for 30 minutes, concentrated, diluted in dioxane and added to a solution of 0.625 g (4.12 mmol) of methyl 4-aminobenzoate and 1 ml (7.5 mmol) of triethylamine in dioxane. The reaction medium is heated at 100° C. for 12 hours, treated with 1N hydrochloric acid solution and extracted with ethyl ether. The residue obtained is purified by chromatography (eluent: 80/20 heptane/ethyl acetate). A solid is obtained (0.73 g; yield=43%; m.p.=147° C.).

c. Synthesis of 4-[2-(8,8-Dimethyl-5-p-tolyl-7,8-dihydro-2-naphthyl)-2-oxoacetylamino]benzoic acid:

In a manner similar to that of Example 22e, by reacting 0.4 g (0.88 mmol) of methyl 4-[2-(8,8-dimethyl-5-p-tolyl-7,8-dihydro-2-naphthyl)-2-oxoacetylamino]benzoate with 0.074 g (1.77 mmol) of lithium hydroxide hydrate, a yellow solid is obtained (0.21 g; yield=56%; m.p.=255° C.).

$^1$H NMR (DMSO) 1.26 (s, 6H); 2.28 (s, 3H); 2.33 (d, 2H, 4.8 Hz); 6.13 (m, 1H); 7.03 (d, 1H, 8.0 Hz); 7.18-7.12 (M, 4H); 7.75 (dd, 2H, 1.6 and 8 Hz); 7.79 (d, 1H, 8.8 Hz); 7.90 (d, 2H, 8.8 Hz); 7.98 (d, 1H, 1.6 Hz).

EXAMPLE 25

Synthesis of 4-[2-(8,8-Dimethyl-5-p-tolyl-7,8-dihydro-2-naphthyl)-2-hydroxyacetylamino]benzoic acid a. Preparation of Methyl (8,8-dimethyl-5-p-tolyl-7,8-dihydro-2-naphthyl)hydroxyacetate:

5 g (18.1 mmol) of 8,8-dimethyl-5-p-tolyl-7,8-dihydro-2-naphthene-carbaldehyde (described in Example 15a) and 2.67 ml (20 mmol) of tetramethylsilyl cyanide are dissolved in 20 ml of acetonitrile, and 2.38 g (25.3 mmol) of lithium tetrafluoroborate are then added. The reaction medium is stirred for 4 hours, hydrolysed and extracted with ethyl acetate. The residue obtained is dissolved in 30 ml of 10N hydrochloric acid and then refluxed for 2 hours. The medium is concentrated, taken up in ethyl ether and concentrated. A solid is obtained (3 g; yield=51%).

b. Preparation of (8,8-Dimethyl-5-p-tolyl-7,8-dihydro-2-naphthyl)hydroxyacetic acid:

In a manner similar to that of Example 22e, by reacting 1.35 g (4 mmol) of methyl (8,8-dimethyl-5-p-tolyl-7,8-dihydro-2-naphthyl)hydroxyacetate with 0.5 g (12 mmol) of lithium hydroxide hydrate, a solid is obtained (1.28 g; yield=99%; m.p.=140° C.).

c. Preparation of Methyl 4-[2-(8,8-dimethyl-5-p-tolyl-7,8-dihydro-2-naphthyl)-2-hydroxyacetylamino]benzoate:

5.44 g (8 mmol) of imidazole are dissolved in 10 ml of dichloromethane at −10° C., and 0.3 ml (4 mmol) of thionyl chloride is then added. After 15 minutes, the medium is added to a solution of 0.605 g (4 mmol) of methyl 4-aminobenzoate in 5 ml of dichloromethane at −40° C. After stirring for 30 minutes while allowing the temperature to rise, the medium is filtered and concentrated. The residue obtained is added to a solution of 1.26 g (3.9 mmol) of (8,8-dimethyl-5-p-tolyl-7,8-dihydro-2-naphthyl)hydroxyacetic acid in 20 ml of acetonitrile, and the medium is then refluxed for 24 hours, concentrated, taken up in 100 ml of ethyl ether and washed with 1N hydrochloric acid solution and with 0.5M sodium hydroxide solution. A yellow solid is obtained (0.94 g; yield=53%).

d. Synthesis of 4-[2-(8,8-Dimethyl-5-p-tolyl-7,8-dihydro-2-naphthyl)-2-hydroxyacetylamino]benzoic acid:

In a manner similar to that of Example 22e, by reacting 0.7 g (1.54 mmol) of methyl 4-[2-(8,8-dimethyl-5-p-tolyl-7,8-dihydro-2-naphthyl)-2-hydroxyacetylamino]benzoate with 0.25 g (6 mmol) of lithium hydroxide hydrate, a solid is obtained (0.68 g; yield=91%; m.p.=145° C.).

$^1$H NMR (DMSO) 1.21 (s, 6H); 2.23 (d, 2H, 4.4 Hz); 2.26 (s, 3H); 5.05 (s, 1H); 5.86 (m, 1H); 6.39 (m, 1H); 6.80 (d, 1H, 8 Hz); 7.19-7.08 (M, 5H); 7.49 (s, 1H); 7.81-7.75 (M, 4H).; 11.00 (s, 1H); 12.60 (s, 1Hz).

EXAMPLE 26

Transactivation Test

The activation of receptors with an agonist (activator) in HeLa cells leads to the expression of a reporter gene, luciferase, which, in the presence of a substrate, generates light. The activation of the receptors may thus be measured by quantifying the luminescence produced after incubating the cells in the presence of a reference agonist. The inhibitory products displace the agonist from its site, thus preventing activation of the receptor. The activity is measured by quantifying the reduction in light produced. This measurement makes it possible to determine the inhibitory activity of the compounds according to the invention.

In this study, a constant is determined which represents the affinity of the molecule for the receptor. Since this value can fluctuate depending on the basal activity and the expression of the receptor, it is referred to as the Kd apparent (KdApp).

To determine this constant, "crossed curves" of the test product against a reference agonist, 4-[2-(5,5,8,8-tetramethyl-5,6,7,8-tetrahydro-2-naphthyl)propenyl]benzoic acid, are performed in 96-well plates. The test product is used at 10 concentrations and the reference agonist at 7 concentrations. In each well, the cells are in contact with a concentration of the test product and a concentration of the reference agonist, 4-[2-(5,5,8,8-tetramethyl-5,6,7,8-tetrahydro-2-naphthyl)propenyl]benzoic acid. Measurements are also taken for the total agonist (4-[2-(5,5,8,8-tetramethyl-5,6,7,8-tetrahydro-2-naphthyl)propenyl]benzoic acid) and inverse agonist, 4-{(E)-3-[4-(4-tert-butylphenyl)-5,5,8,8-tetramethyl-5,6,7,8-tetrahydro-2-naphthyl]-3-oxopropenyl}benzoic acid, controls.

These crossed curves make it possible to determine the $AC_{50}$ values (concentration at which 50% activation is observed) for the reference ligand at various concentrations of test product. These $AC_{50}$ values are used to calculate the Schild regression by plotting a straight line corresponding to the Schild equation ("quantitation in receptor pharmacology" Terry P. Kenakin, *Receptors and Channels*, 2001, 7, 371-385).

In the case of an antagonist, an $IC_{50}$ value (concentration that inhibits 50% of the activity) is calculated by plotting the curve of the product at the concentration of the reference ligand that gives 80% activation.

The HeLa cell lines used are stable transfectants containing the plasmids ERE-βGlob-Luc-SV-Neo (reporter gene) and RAR (α, β, γ) ER-DBD-puro. These cells are inoculated into 96-well plates at a rate of 10 000 cells per well in 100 μl of DMEM medium without phenol red, and supplemented with 10% defatted calf serum. The plates are then incubated at 37° C. and 7% $CO_2$ for 4 hours.

The various dilutions of the test products, of the reference ligand (4-[2-(5,5,8,8-tetramethyl-5,6,7,8-tetrahydro-2-naphthyl)propenyl]benzoic acid), of the 100% control (100 nM 4-[2-(5,5,8,8-tetramethyl-5,6,7,8-tetrahydro-2-naphthyl)propenyl]benzoic acid) and of the 0% control (500 nM 4-{(E)-3-[4-(4-tert-butylphenyl)-5,5,8,8-tetramethyl-5,6,7,8-tetrahydro-2-naphthyl]-3-oxopropenyl}benzoic acid) are added at a rate of 5 μl per well. The plates are then incubated for 18 hours at 37° C. and 7% $CO_2$.

The culture medium is removed by turning over and 100 μl of a 1:1 PBS/luciferine mixture is added to each well. After 5 minutes, the plates are read using the luminescence reader.

|  | RAR alpha | | RAR beta | | RAR gamma | |
|---|---|---|---|---|---|---|
|  | Kdapp (nM) | $IC_{50}$ (nM) | Kdapp (nM) | $IC_{50}$ (nM) | Kdapp (nM) | $IC_{50}$ (nM) |
| Ex 1 | 30 | 52.5 | 8 | 12.8 | 2 | 5 |
| Ex 9 | 120 | 210 | 8 | 12.8 | 2 | 5 |
| Ex 19 | 500 | 875 | 120 | 192 | 60 | 150 |

The results obtained with the compounds according to the invention clearly show Kdapp values ≦100 nM and an $IC_{50}$ value ≦150 nM for at least one of the receptor subtypes, this clearly demonstrating a reduction in the signal, and in the luminescence in the presence of the reference agonist. The compounds according to the invention are thus clearly inhibitors of retinoic acid receptors (RAR).

EXAMPLE 27

Formulation Examples

This example illustrates various specific formulations based on the compounds according to the invention.

A - ORAL ROUTE:

(a) 0.2 g tablet:

| | |
|---|---|
| Compound of Example 16 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampoules:

| | |
|---|---|
| Compound of Example 17 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g tablet:

| | |
|---|---|
| Compound of Example 9 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampoules:

| | |
|---|---|
| Compound of Example 2 | 0.200 g |
| Glycerol | 1.000 g |
| 70% sorbitol | 1.000 g |
| Sodium saccharinate | 0.010 g |
| Methyl para-hydroxybenzoate | 0.080 g |
| Flavoring | qs |
| Purified water | qs 10 ml |

B - PARENTERAL ROUTE:

(a) Composition:

| | |
|---|---|
| Compound of Example 3 | 0.002 g |
| Ethyl oleate | qs 10 g |

-continued (b) Composition:

| | | |
|---|---|---|
| Compound of Example 1 | 0.05% | |
| Polyethylene glycol | 20% | |
| 0.9% NaCl solution | qs 100 | |

(c) Composition:

| | | |
|---|---|---|
| Compound of Example 3 | 2.5% | |
| Polyethylene glycol 400 | 20% | |
| 0.9% NaCl solution | qs 100 | |

(d) Injectable cyclodextrin composition:

| | | |
|---|---|---|
| Compound of Example 3 | 0.1 mg | |
| β-Cyclodextrin | 0.10 g | |
| Water for injection | qs 10.00 g | |

C - TOPICAL ROUTE:

(a) Ointment:

| | |
|---|---|
| Compound of Example 12 | 0.020 g |
| Isopropyl myristate | 81.700 g |
| Liquid petroleum jelly fluid | 9.100 g |
| Silica ("Aerosil 200" sold by Degussa) | 9.180 g |

(b) Ointment:

| | |
|---|---|
| Compound of Example 15 | 0.300 g |
| White petroleum jelly codex | qs 100 g |

(c) Nonionic water-in-oil cream:

| | |
|---|---|
| Compound of Example 10 | 0.100 g |
| Mixture of emulsifying lanolin alcohols, waxes and oils ("Anhydrous Eucerin" sold by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:

| | |
|---|---|
| Compound of Example 9 | 0.100 g |
| Polyethylene glycol (PEG 400) | 69.900 g |
| 95% ethanol | 30.000 g |

(e) Hydrophobic ointment:

| | |
|---|---|
| Compound of Example 4 | 0.300 g |
| Isopropyl myristate | 36.400 g |
| Silicone oil ("Rhodorsil 47 V 300" sold by Rhône-Poulenc) | 36.400 g |
| Beeswax | 13.600 g |
| Silicone oil ("Abil 300 000 cst" sold by Goldschmidt) | qs 100 g |

(f) Nonionic oil-in-water cream:

| | |
|---|---|
| Compound of Example 6 | 1.000 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structural formula (I):

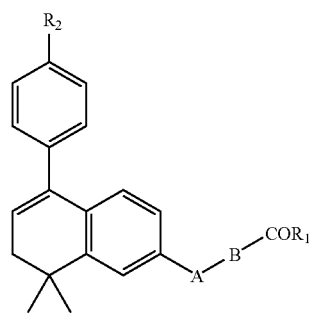

(I)

in which A is a CHOH, C=O or C=N—OH radical or a sulfur or selenium atom; B is a radical selected from among those of formulae (a) to (f):

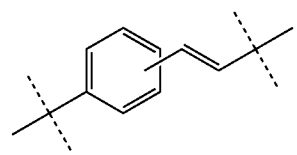

(a)

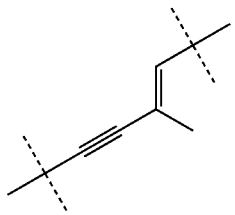

(b)

(c)

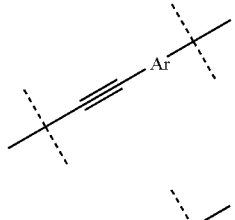

(d)

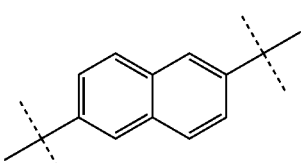

(e)

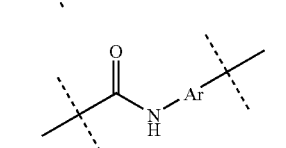

(f)

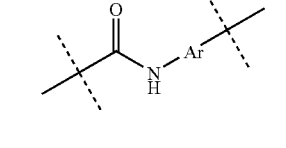

Ar is a radical selected from among those of formulae (g) to (i):

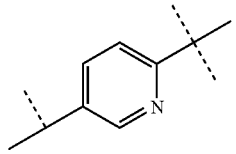
(g)

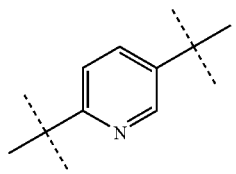
(h)

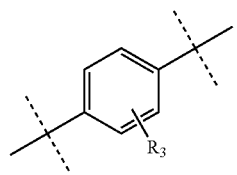
(i)

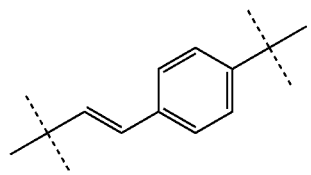

wherein $R_3$ is as defined below; $R_1$ is a radical —OH, —$OR_4$, —$NHR_5$ or $NR_5R_6$, wherein $R_4$, $R_5$ and $R_6$ are as defined below; $R_2$ is a hydrogen, fluorine, chlorine or bromine atom, a linear or branched alkyl radical having 1 to 5 carbon atoms, a $CF_3$, $OR_7$, $SR_7$, $NHR_8$, $NR_8R_9$, 2-naphthyl, 2-pyridyl, 3-pyridyl, 4-pyridyl, 2-thiophenyl, $CH_2OR_{10}$ or $CH_2NR_{11}R_{12}$ radical or a phenyl radical which is unsubstituted or substituted with at least one fluorine atom or with a methyl, ethyl, isopropyl, tert-butyl or $CF_3$ radical, wherein $R_7$, $R_8$, $R_9$, $R_{10}$, $R_{11}$ and $R_{12}$ are as defined below; $R_3$ is a hydrogen, fluorine or chlorine atom or a radical OH, $OR_{13}$, $CF_3$ or $NR_{14}R_{15}$, wherein $R_{13}$, $R_{14}$ and $R_{15}$ are as defined below; $R_4$ is a linear or branched alkyl radical having 1 to 4 carbon atoms; $R_5$ is a hydrogen atom, an OH group or a linear or branched alkyl radical having 1 to 4 carbon atoms; $R_6$ is a linear or branched alkyl radical having 1 to 4 carbon atoms; $R_7$ is a hydrogen atom, a linear or branched alkyl radical having 1 to 6 carbon atoms, a radical $CH_2OR_{16}$ or a benzyl radical which is unsubstituted or substituted with at least one halogen atom, or with a methyl, ethyl, isopropyl, tert-butyl or $CF_3$ radical, wherein $R_{16}$ is as defined below; $R_8$, $R_9$, $R_{11}$, $R_{12}$, $R_{14}$ and $R_{15}$, which may be identical or different, are each a hydrogen atom, a linear or branched alkyl radical having 1 to 4 carbon atoms, (C=O)—$R_{17}$ or (C=O)—$OR_{17}$, wherein $R_{17}$ is as defined below; $R_{10}$ is a linear or branched alkyl radical having 1 to 4 carbon atoms or a benzyl or phenyl radical optionally substituted by one halogen atom, or by one alkyl radical having 1 to 3 carbon atoms; $R_{13}$ is a methyl, ethyl or acetyl radical; $R_{16}$ is a methyl, ethyl or $CH_2CH_2OCH_3$ radical; $R_{17}$ is a hydrogen atom or a linear or branched alkyl radical having 1 to 4 carbon atoms; and the stereoisomers and optical or geometrical isomers or mixtures thereof, and the salts obtained with a pharmaceutically acceptable acid or base, with the proviso that, when A is a C=O radical, then B cannot have the formula (d):

2. The compound as defined by claim 1, wherein formula (I), A is a CHOH radical.
3. The compound as defined by claim 1, wherein formula (I), A is a C=O radical.
4. The compound as defined by claim 1, wherein formula (I), A is a C=N—OH radical.
5. The compound as defined by claim 1, wherein formula (I), A is a sulfur atom.
6. The compound as defined by claim 1, wherein formula (I), A is a selenium atom.
7. The compound as defined by claim 1, wherein formula (I), B is a radical (a).
8. The compound as defined by claim 1, wherein formula (I), B is a radical (b).
9. The compound as defined by claim 1, wherein formula (I), B is a radical (c).
10. The compound as defined by claim 1, wherein formula (I), B is a radical (d).
11. The compound as defined by claim 1, wherein formula (I), B is a radical (e).
12. The compound as defined by claim 1, wherein formula (I), B is a radical (f).
13. The compound as defined by claim 1, wherein formula (I), Ar is a radical (g).
14. The compound as defined by claim 1, wherein formula (I), Ar is a radical (h).
15. The compound as defined by claim 1, wherein formula (I), Ar is a radical (i).
16. The compound as defined by claim 1, selected from the group consisting of:
   1. 4-(8,8-dimethyl-5-p-tolyl-7,8-dihydro-2-naphthylselanylethynyl)benzoic acid,
   2. 5-(8,8-dimethyl-5-p-tolyl-7,8-dihydro-2-naphthylselanyl)-3-methylpent-2-en-4-ynoic acid,
   3. 4-[5-(4-tert-butylphenyl)-8,8-dimethyl-7,8-dihydro-2-naphthylselanylethynyl]benzoic acid,
   4. 5-[5-(4-tert-butylphenyl)-8,8-dimethyl-7,8-dihydro-2-naphthylselanyl]-3-methylpent-2-en-4-ynoic acid,
   5. 4-(8,8-dimethyl-5-p-tolyl-7,8-dihydro-2-naphthylselanylethynyl)-2-methoxybenzoic acid,
   6. 4-(8,8-dimethyl-5-p-tolyl-7,8-dihydro-2-naphthylselanylethynyl)-2-hydroxybenzoic acid,
   7. 4-[5-(4-methoxyphenyl)-8,8-dimethyl-7,8-dihydro-2-naphthylselanylethynyl]benzoic acid,
   8. 6-(8,8-dimethyl-5-p-tolyl-7,8-dihydro-2-naphthylselanylethynyl)nicotinic acid,
   9. 4-(8,8-dimethyl-5-p-tolyl-7,8-dihydro-2-naphthylselanylethynyl)-2-fluorobenzoic acid,
   10. (E)-3-[4-(8,8-dimethyl-5-p-tolyl-7,8-dihydro-2-naphthylselanyl)phenyl]acrylic acid,
   11. (Z)-3-[3-(8,8-dimethyl-5-p-tolyl-7,8-dihydro-2-naphthylselanyl)phenyl]acrylic acid,
   12. 3-{4-[5-(4-tert-butylphenyl)-8,8-dimethyl-7,8-dihydro-2-naphthylselanyl]phenyl}acrylic acid,
   13. 3-{3-[5-(4-tert-butylphenyl)-8,8-dimethyl-7,8-dihydro-2-naphthylselanyl]phenyl}acrylic acid, 14. 6-(8,8-dimethyl-5-p-tolyl-7,8-dihydro-2-naphthylselanyl)naphthalene-2-carboxylic acid,
15. 4-[3-(8,8-dimethyl-5-p-tolyl-7,8-dihydro-2-naphthyl)-3-hydroxyprop-1-ynyl]benzoic acid,
16. 4-[3-(8,8-dimethyl-5-p-tolyl-7,8-dihydro-2-naphthyl)-3-hydroxyprop-1-ynyl]-2-hydroxybenzoic acid,
17. 4-{3-[5-(4-ethoxymethoxyphenyl)-8,8-dimethyl-7,8-dihydro-2-naphthyl]-3-hydroxyprop-1-ynyl}benzoic acid,
18. 4-{3-[5-(4-benzyloxyphenyl)-8,8-dimethyl-7,8-dihydro-2-naphthyl]-3-hydroxyprop-1-ynyl}benzoic acid,
19. 4-{3-[5-(4-dimethylaminophenyl)-8,8-dimethyl-7,8-dihydro-2-naphthyl]-3-hydroxyprop-1-ynyl}benzoic acid,
20. 4-[3-(8,8-dimethyl-5-p-tolyl-7,8-dihydro-2-naphthyl)-3-oxoprop-1-ynyl]benzoic acid,
21. 4-[3-(8,8-dimethyl-5-p-tolyl-7,8-dihydro-2-naphthyl)-3-hydroxypropenyl]benzoic acid,
22. 6-[(8,8-dimethyl-5-p-tolyl-7,8-dihydro-2-naphthyl)-hydroxymethyl]naphthalene-2-carboxylic acid,
23. 6-(8,8-dimethyl-5-p-tolyl-7,8-dihydro-2-naphthylcarbonyl)naphthalene-2-carboxylic acid,
24. 4-[2-(8,8-dimethyl-5-p-tolyl-7,8-dihydro-2-naphthyl)-2-oxoacetylamino]benzoic acid,
25. 4-[2-(8,8-dimethyl-5-p-tolyl-7,8-dihydro-2-naphthyl)-2-hydroxyacetylamino]benzoic acid,
26. ethyl 4-[3-(8,8-dimethyl-5-p-tolyl-7,8-dihydro-2-naphthyl)-3-hydroxyprop-1-ynyl]benzoate,
27. isobutyl 4-[3-(8,8-dimethyl-5-p-tolyl-7,8-dihydro-2-naphthyl)-3-hydroxyprop-1-ynyl]benzoate,
28. 4-[3-(8,8-dimethyl-5-p-tolyl-7,8-dihydro-2-naphthyl)-3-hydroxyprop-1-ynyl]-N-hydroxybenzamide,
29. 4-[3-(8,8-dimethyl-5-p-tolyl-7,8-dihydro-2-naphthyl)-3-hydroxyprop-1-ynyl]-N,N-dimethylbenzamide,
30. 4-[3-(8,8-dimethyl-5-p-tolyl-7,8-dihydro-2-naphthyl)-3-hydroxyprop-1-ynyl]-N-methylbenzamide,
31. 4-[3-(8,8-dimethyl-5-p-tolyl-7,8-dihydro-2-naphthyl)-3-hydroxyprop-1-ynyl]-N-isobutylbenzamide,
32. 4-[3-(8,8-dimethyl-5-p-tolyl-7,8-dihydro-2-naphthyl)-3-hydroxyprop-1-ynyl]-N-isobutyl-N-methylbenzamide,
33. isobutyl 4-(8,8-dimethyl-5-p-tolyl-7,8-dihydro-2-naphthylselanylethynyl)benzoate,
34. 4-(5-biphenyl-4-yl-8,8-dimethyl-7,8-dihydro-2-naphthylselanylethynyl)benzoic acid,
35. 4-[3-(5-biphenyl-4-yl-8,8-dimethyl-7,8-dihydro-2-naphthyl)-3-hydroxyprop-1-ynyl]benzoic acid,
36. 4-{3-[8,8-dimethyl-5-(4-pyrid-2-ylphenyl)-7,8-dihydro-2-naphthyl]-3-hydroxyprop-1-ynyl}benzoic acid,
37. 4-[8,8-dimethyl-5-(4-pyrid-2-ylphenyl)-7,8-dihydro-2-naphthylselanylethynyl]benzoic acid,
38. 4-[8,8-dimethyl-5-(4-thiophen-2-ylphenyl)-7,8-dihydro-2-naphthylselanylethynyl]benzoic acid,
39. 4-{3-hydroxy-3-[5-(4-methoxymethylphenyl)-8,8-dimethyl-7,8-dihydro-2-naphthyl]prop-1-ynyl}benzoic acid,
40. 4-[5-(4-methoxymethylphenyl)-8,8-dimethyl-7,8-dihydro-2-naphthylselanylethynyl]benzoic acid,
41. 4-[8,8-dimethyl-5-(4-phenoxymethylphenyl)-7,8-dihydro-2-naphthylselanylethynyl]benzoic acid,
42. 4-{3-[8,8-dimethyl-5-(4-phenoxymethylphenyl)-7,8-dihydro-2-naphthyl]-3-hydroxyprop-1-ynyl}benzoic acid,
43. 4-(3-{5-[4-(4-fluorophenoxymethyl)phenyl]-8,8-dimethyl-7,8-dihydro-2-naphthyl}-3-hydroxyprop-1-ynyl)benzoic acid,
44. 4-{5-[4-(4-fluorophenoxymethyl)phenyl]-8,8-dimethyl-7,8-dihydro-2-naphthylselanylethynyl}benzoic acid,
45. 4-[5-(4-dimethylaminomethylphenyl)-8,8-dimethyl-7,8-dihydro-2-naphthylselanylethynyl]benzoic acid,
46. 4-{3-[5-(4-dimethylaminomethylphenyl)-8,8-dimethyl-7,8-dihydro-2-naphthyl]-3-hydroxyprop-1-ynyl}benzoic acid,
47. 4-[3-(5-{4-[(acetylmethylamino)methyl]phenyl}-8,8-dimethyl-7,8-dihydro-2-naphthyl)-3-hydroxyprop-1-ynyl]benzoic acid,
48. 4-(5-{4-[(acetylmethylamino)methyl]phenyl}-8,8-dimethyl-7,8-dihydro-2-naphthylselanylethynyl)benzoic acid,
49. 4-[5-(4-acetylaminophenyl)-8,8-dimethyl-7,8-dihydro-2-naphthylselanylethynyl]benzoic acid,
50. 4-{3-[5-(4-tert-butoxycarbonylaminophenyl)-8,8-dimethyl-7,8-dihydro-2-naphthyl]-3-hydroxyprop-1-ynyl}benzoic acid,
51. 4-(3-{5-[4-(tert-butoxycarbonylmethylamino)phenyl]-8,8-dimethyl-7,8-dihydro-2-naphthyl}-3-hydroxyprop-1-ynyl)benzoic acid,
52. 4-{5-[4-(tert-butoxycarbonylmethylamino)phenyl]-8,8-dimethyl-7,8-dihydro-2-naphthylselanylethynyl}benzoic acid,
53. 4-[5-(4-tert-butoxycarbonylaminophenyl)-8,8-dimethyl-7,8-dihydro-2-naphthylselanylethynyl]benzoic acid,
54. 4-{5-[4-(4-fluorobenzyloxy)phenyl]-8,8-dimethyl-7,8-dihydro-2-naphthylselanylethynyl}benzoic acid,
55. 4-(3-{5-[4-(4-fluorobenzyloxy)phenyl]-8,8-dimethyl-7,8-dihydro-2-naphthyl}-3-hydroxyprop-1-ynyl)benzoic acid,
56. 4-{3-[5-(4-benzylsulfanylphenyl)-8,8-dimethyl-7,8-dihydro-2-naphthyl]-3-hydroxyprop-1-ynyl}benzoic acid,
57. 4-[5-(4-benzylsulfanylphenyl)-8,8-dimethyl-7,8-dihydro-2-naphthylselanylethynyl]benzoic acid,
58. 4-{3-hydroxy-3-[5-(4-thiophen-2-ylphenyl)-8,8-dimethyl-7,8-dihydro-2-naphthyl]prop-1-ynyl}benzoic acid,
59. 4-{3-[5-(4-acetylaminophenyl)-8,8-dimethyl-7,8-dihydro-2-naphthyl]-3-hydroxyprop-1-ynyl}benzoic acid,
60. (S)-4-[3-(8,8-dimethyl-5-p-tolyl-7,8-dihydro-2-naphthyl)-3-hydroxyprop-1-ynyl]benzoic acid,
61. (R)-4-[3-(8,8-dimethyl-5-p-tolyl-7,8-dihydro-2-naphthyl)-3-hydroxyprop-1-ynyl]benzoic acid, and mixtures thereof.

17. An alkali or alkaline-earth metal or zinc salt, or organic amine salt of the compound as defined by claim 1.

18. A regime or regimen for treating a dermatological condition or affliction by inhibiting RAR receptors, comprising administering to a mammalian organism in need of such treatment a thus effective amount of a compound as defined by claim 1.

19. The regime or regimen as defined by claim 18, comprising treating a mammalian organism afflicted with common acne, comedones, polymorphs, acne rosacea, nodulocystic acne, acne conglobata, senile acne, secondary acne, solar acne, medication-related acne or occupational acne.

20. The regime or regimen as defined by claim 18, comprising treating a mammalian organism afflicted with ichthyosis, an ichthyosiform condition, Darier's disease, palmoplantar keratoderma, leukoplakia, a leukoplakiform condition, or cutaneous or mucous (buccal) lichen.

21. The regime or regimen as defined by claim 18, comprising treating a mammalian organism afflicted with psoriasis, whether cutaneous, mucous or ungual, psoriatic rheumatism, cutaneous atopy, eczema, respiratory atopy, or gingival hypertrophy.

22. A regime or regimen for treating dermal or epidermal proliferations by inhibiting RAR receptors, whether benign or malignant and whether or not of viral origin, comprising administering to a mammalian organism in need of such treatment a thus effective amount of a compound as defined by claim 1.

23. The regime or regimen as defined by claim 22, comprising treating a mammalian organism afflicted with common warts, flat warts, verruciform epidermodysplasia, oral or florid papillomatoses, T lymphoma, proliferations induced by ultraviolet radiation, basocellular or spinocellular epithelioma, any cutaneous precancerous lesion or a keratoacanthoma.

24. The regime or regimen as defined by claim 18, comprising treating a mammalian organism afflicted with immune dermatosis, lupus erythematosus, an immune bullous or collagen disease, or scleroderma.

25. A regime or regimen for treating a dermatological condition or affliction having an immunological component by inhibiting RAR receptors, comprising administering to a mammalian organism in need of such treatment a thus effective amount of a compound as defined by claim 1.

26. A regime or regimen for treating an ophthalmological disorder or corneopathy by inhibiting RAR receptors, comprising administering to a mammalian organism in need of such treatment a thus effective amount of a compound as defined by claim 1.

27. A regime or regimen for treating the stigmata of epidermal and/or dermal atrophy by inhibiting RAR receptors, or any other form of cutaneous atrophy, comprising administering to a mammalian organism in need of such treatment a thus effective amount of a compound as defined by claim 1.

28. A regime or regimen for treating a cutaneous condition or affliction of viral origin by inhibiting RAR receptors, comprising administering to a mammalian organism in need of such treatment a thus effective amount of a compound as defined by claim 1.

29. A regime or regimen for treating a skin condition or affliction associated with chronological or actinic aging by inhibiting RAR receptors, comprising administering to a mammalian organism in need of such treatment a thus effective amount of a compound as defined by claim 1.

30. The regime or regimen as defined by claim 29, comprising treating a mammalian organism afflicted with excess pigmentation, actinic keratosis or xerosis.

31. A regime or regimen for treating a sebaceous function disorder, comprising administering to a mammalian organism in need of such treatment a thus effective amount of a compound as defined by claim 1.

32. The regime or regimen as defined by claim 21, comprising treating a mammalian organism afflicted with the hypersborrhoea of acne or simple seborrhoea.

33. A regime or regimen for preventing or treating a cicatrization disorder by inhibiting RAR receptors, or for preventing or repairing stretch marks, or for promoting cicatrization, comprising administering to a mammalian organism in need of such treatment a thus effective amount of a compound as defined by claim 1.

34. A regime or regimen for treating a skin pigmentation disorder by inhibiting RAR receptors, comprising administering to a mammalian organism in need of such treatment a thus effective amount of a compound as defined by claim 1.

35. The regime or regimen as defined by claim 34, comprising treating a mammalian organism afflicted with hyperpigmentation, melasma, hypopigmentation or vitiligo.

36. A regime or regimen for treating a cancerous or precancerous condition or affliction by inhibiting RAR receptors, comprising administering to a mammalian organism in need of such treatment a thus effective amount of a compound as defined by claim 1.

37. A regime or regimen for treating a disorder of the immune system by inhibiting RAR receptors, comprising administering to a mammalian organism in need of such treatment a thus effective amount of a compound as defined by claim 1.

38. A pharmaceutical composition comprising a therapeutically effective amount of at least one compound as defined by claim 1, or salt or isomer thereof, formulated into a physiologically acceptable medium therefor.

39. The pharmaceutical composition as defined by claim 38, said at least one compound, or salt or isomer, comprising from 0.001% to 10% by weight thereof.

40. The pharmaceutical composition as defined by claim 38, said at least one compound, or salt or isomer, comprising from 0.01% to 1% by weight thereof.

41. A cosmetic composition comprising a cosmetic effective amount of at least one compound as defined by claim 1, or salt or isomer thereof, formulated into a cosmetically acceptable medium therefor.

42. The cosmetic composition as defined by claim 41, said at least one compound, or salt or isomer, comprising from 0.001% to 3% by weight thereof.

43. The pharmaceutical composition as defined by claim 38, formulated as a paste, an ointment, a cream, a milk, a pomade, a powder, an impregnated pad, a syndet, a gel, a spray, a mousse, a stick, a shampoo, microspheres, nanospheres, lipid or polymer vesicles, a controlled release patch, a syrup, tablets, capsules, granules, an emulsion, or a dragee.

* * * * *